United States Patent [19]

Jameson et al.

[11] Patent Number: 5,360,320

[45] Date of Patent: Nov. 1, 1994

[54] MULTIPLE SOLVENT DELIVERY SYSTEM

[75] Inventors: Daniel G. Jameson; Robert W. Allington, both of Lincoln, Nebr.

[73] Assignee: Isco, Inc., Lincoln, Nebr.

[21] Appl. No.: 843,624

[22] Filed: Feb. 27, 1992

[51] Int. Cl.$^5$ ............................................. F04B 41/06
[52] U.S. Cl. ............................................ 417/4; 417/5; 417/44.2; 417/53
[58] Field of Search ................... 417/2, 3, 4, 5, 6, 7, 417/18, 44 A, 53, 63, 45

[56] References Cited

U.S. PATENT DOCUMENTS

| 4,714,545 | 12/1987 | Bente et al. | 417/5 |
| 4,913,624 | 4/1990 | Seki | 417/2 |
| 4,915,591 | 4/1990 | Funke | 417/63 |

Primary Examiner—Richard A. Bertsch
Assistant Examiner—Roland G. McAndrews
Attorney, Agent, or Firm—Vincent L. Carney

[57] ABSTRACT

To control a solvent composition in a supercritical fluid system, a first pump pumps a first solvent through a first conduit into a mixer and a second pump pumps a second solvent through a second conduit into the mixer. First and second transducers measure the pressure in the first and second conduits and generate first and second signals proportional to the pressures. Each pressure signal is multiplied by a corresponding programmed concentration signal and compared to the programmed pressure in a feedback system to generate an error signal. The error signal is multiplied by concentration signals from a programmer to control the pumping rate of each pump. The pumps pressurize each fluid one at a time at the start of a run. The pressurization process is also used for producing disturbance-free flow as delivery is changed from one pump to another during prolonged runs.

22 Claims, 7 Drawing Sheets

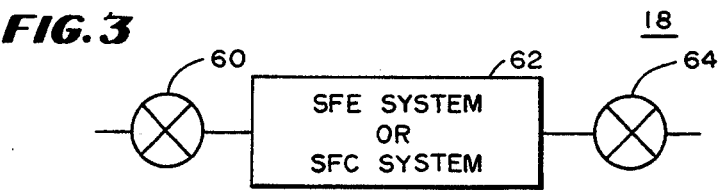
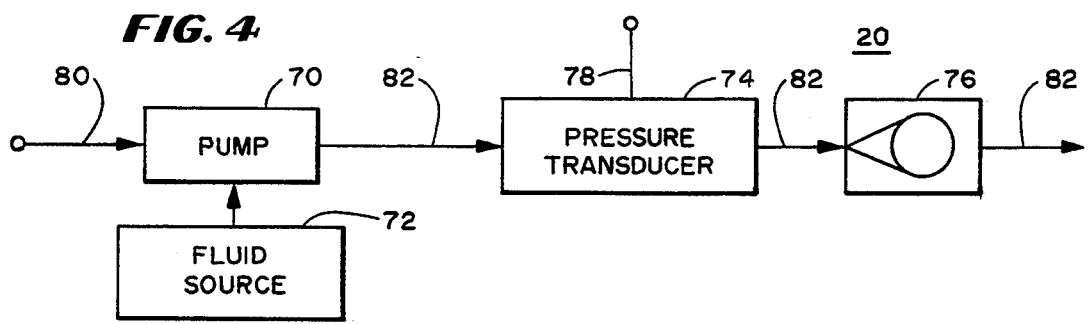
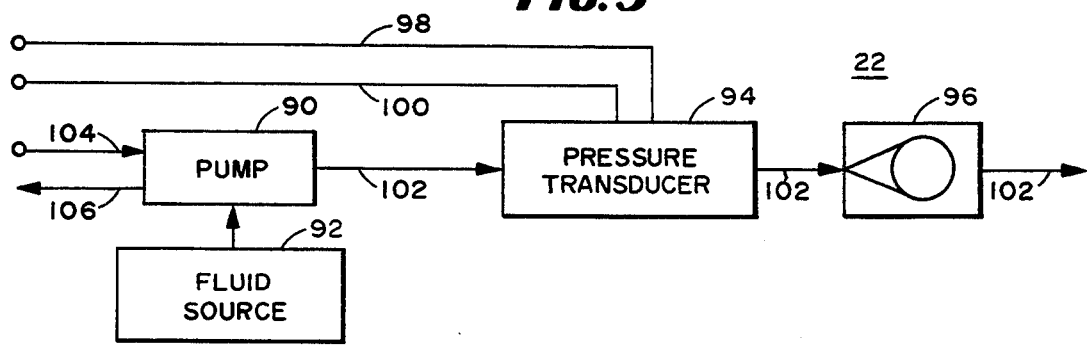
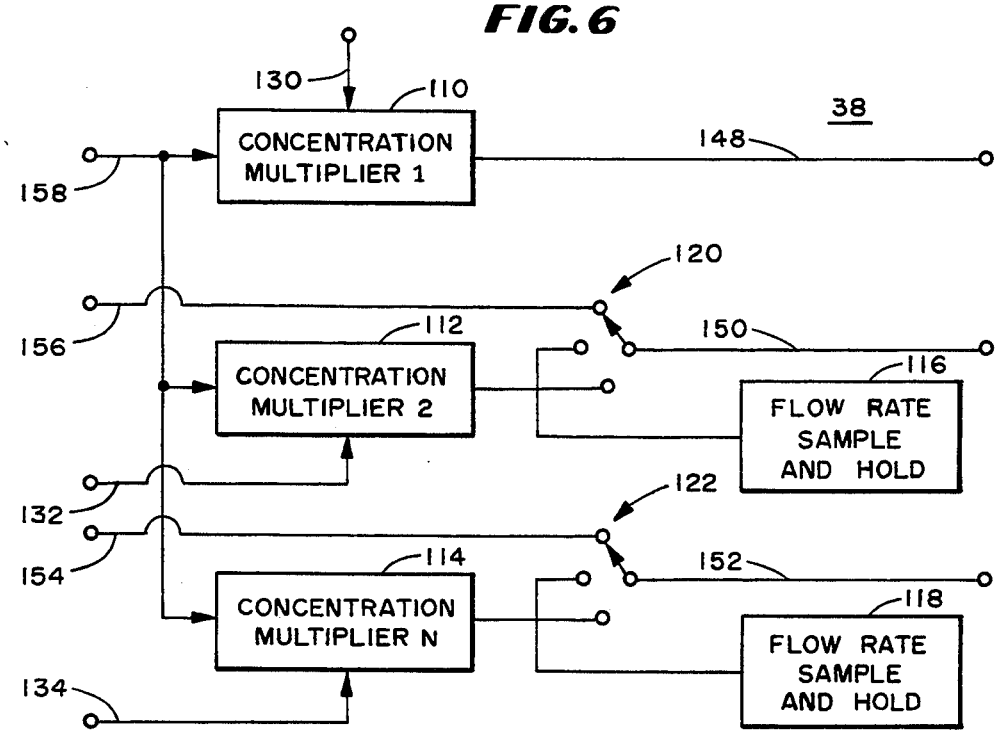

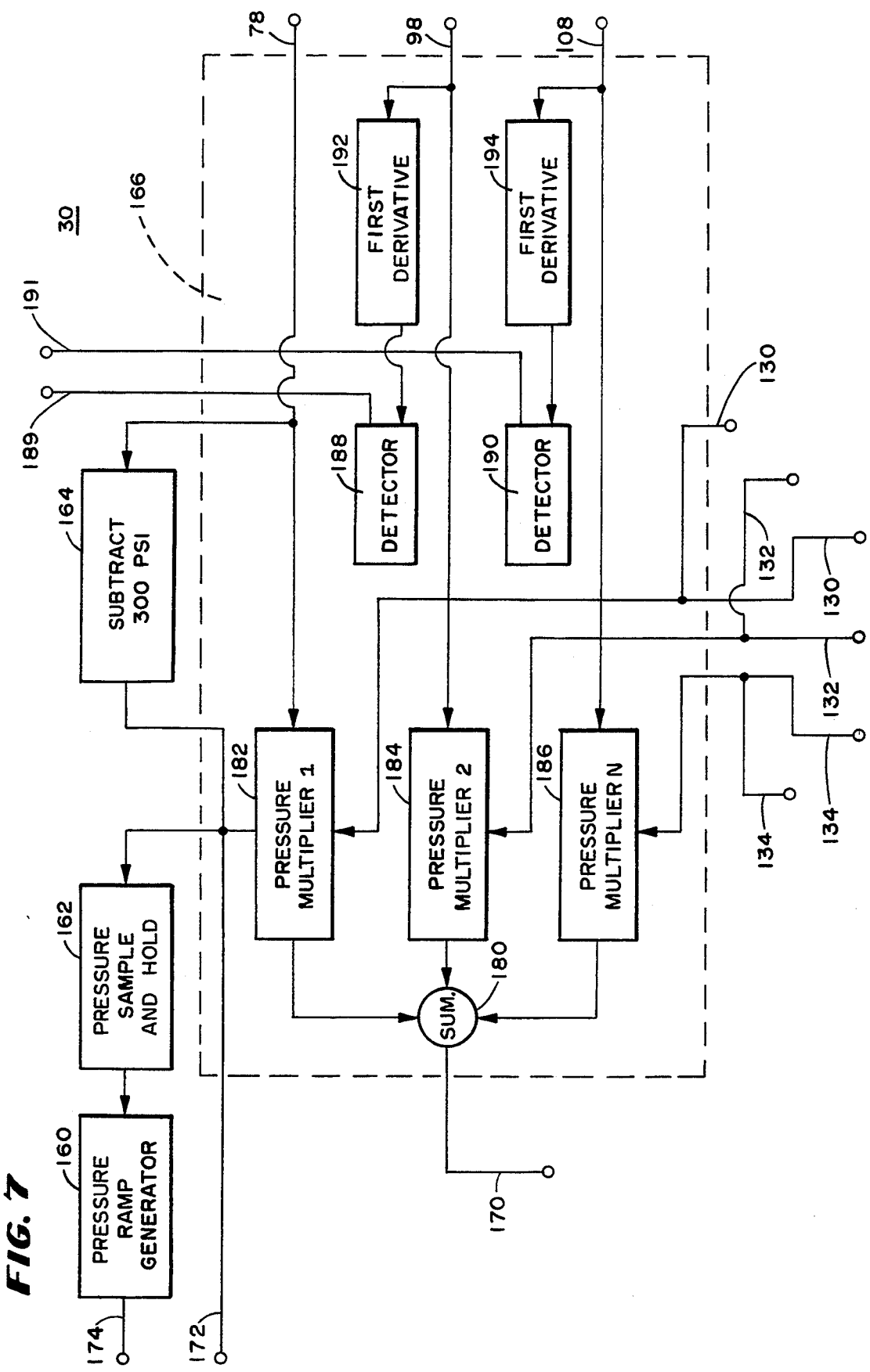

MULTIPLE SOLVENT DELIVERY SYSTEM

BACKGROUND OF THE INVENTION

This invention relates to multiple pump fluid delivery systems, such as for example, systems used to deliver multiple different solvents to columns in gradient elution liquid chromatography or to pressure vessels in fluid extraction or systems used to switch the outlet flow from one syringe pump to another to provide continuous flow without interruption or fluid disturbance.

In one class of multiple pump fluid delivery system, an effort is made to control the pressure of the fluids delivered to a vessel or column and in some such pressure controlled systems to also control the composition such as for example the ratio of the different fluids. In some such systems using controlled pressure and composition, the flow rate is controlled from each of a plurality of different pumps. The pressure is measured by transducers and one or more signals fed back to control the pumping motors and thus to maintain the proper flow rate for the desired composition and the proper pressure. These systems are of particular significance in supercritical fluid chromatography and supercritical fluid extraction systems using multiple solvents.

In one prior art system of this type, disclosed in U.S. Pat. No. 5,071,562, two syringe pumps for two different fluids are independently controlled for flow rate by a gradient controller and the pressures are equalized between the two pumps by a mechanical mixer which permits only the first or primary fluid to flow at the programmed rate while the second pump under program control builds up pressure to equal the pressure of the first pump so that a uniform pressure is applied to the fluids mixed in the mixer as they flow to the chromatographic column. The pressure equalizing mechanism is combined in mechanical structure with the mixer.

This system is relatively complex and suitable for only two pumps. It is known to control instability using feedback circuitry. One such system which controls transient instability in a single fluid flow system including a syringe pump is disclosed in U.S. Pat. No. 4,043,906 to Helmet. This system utilizes a multiple degree feedback system to provide adequate damping against transients. There is no disclosure of how to adapt this system to a multiple solvent system which controls pressure so as to maintain stability while at the same time providing the proper composition. This is a particularly significant problem when using supercritical fluids because of their compressibility.

In another prior art system, disclosed in U.S. Pat. No. 4,347,131 filed in the name of Brownlee, a continuously flowing pumping system with mechanically operated valves is disclosed. This system uses two syringe pumps which operate reciprocally. However, there is no disclosure on how the valves or other parts of the system may be automatically operated to transfer flow from one pump to another without disturbance. A similar pump has been sold commercially in the United States by Chromatramix, Inc.

Generally, pressure transducers are not well enough matched in accuracy to measure pressure at multiple points in the fluid system to be used to control valves automatically for the prevention of the transfer of fluid flow from one pump to the next without disturbance.

SUMMARY OF THE INVENTION

Accordingly, it is an object of the invention to provide a novel system for controlling the delivery of fluids.

It is a still further object of the invention to provide a novel multiple fluid delivery system.

It is a still further object of the invention to provide a multi-solvent system which is expandable to any number of fluids pumped by any number of pumps.

It is a still further object of the invention to provide a multiple solvent delivery system in which the composition, pressure or flow rate of the solvent mixture is controlled.

It is a still further object of the invention to provide a novel multiple liquid delivery system in which it is unnecessary to have a pressure transducer monitoring the mixture of liquids and only necessary to have one pressure transducer monitoring each of the components being pumped into the mixture.

It is a still further object of the invention to accomplish the foregoing objects with syringe pumps.

It is still a further object of the invention to provide a disturbance-free transfer of flow from one pump to another, using a pressure transducer or transducers of ordinary precision, and thus to provide a continuously flowing pumping system.

In accordance with the above and further objects of the invention, a multiple fluid delivery system includes a plurality of pumps pumping a plurality of different fluids into a mixer under the control of a gradient control system that controls the proportions of the fluids. The pressure of each flow stream is monitored on the upstream side of a check valve and the monitored pressure used to provide feedback to control the pumping rates in accordance with both the composition of the final solution and the pressure. A valve is connected in the conduit communicating with the inlet port of the column or extraction vessel and a different valve is connected in the conduit communicating with the outlet port of the column or extraction vessel.

Thus, the speed of pumping is controlled for each of the pumps to provide the proper composition, with initial amounts of fluid being controlled to provide the programmed pressure without fluctuations caused by the pressure of the fluid from one pump being greater than the fluid from another pump. This system also controls the composition and pressure of the mixture while avoiding backflow problems by controlling the rate of pumping of each of the fluids forming the composition. Preferably, syringe type pumps are utilized in which the rate of movement of the syringe type pump is controlled in accordance with the amount of fluid to be contributed to the mixture. However, the elasticity or compressibility and mobility of the fluid within syringe pumps makes it difficult to avoid backflow into one of the pumps during pressurization. It is more difficult if the timing has to be controlled and no significant pressure anomalies are allowable.

In operation, the primary fluid is first pumped with the valves communicating with the inlet and outlet ports of the column or extraction vessel closed. If only one fluid is to be used, the upstream valve may be opened at the time the desired pressure is reached and then the downstream valve opened and the pump speed controlled thereafter to maintain that pressure. The pump may be controlled by a feedback circuit from a transducer in the flow stream that measures the pressure at which the fluid is being delivered.

When a plurality of different fluids are being pumped into the mixture to form the final composition of fluids, the system is pressurized first with the primary fluid and the upstream and downstream valves to the column or extraction vessel closed. The valve upstream to the column or extraction vessel is then opened and the system repressurized with the primary fluid. The valve upstream to the column or extraction vessel is opened manually in some embodiments and automatically in others by sensing the stabilization of the rate of change of pressure or that the magnitude of the pressure error is less than a threshold value.

When the valve to the pressure vessel or chromatographic column or other receiving unit is opened, a dip in pressure may be sensed in the primary fluid flow path. This instability is cured by controlling the pump speed of the primary pump before other pumps begin increasing their pressure. In a completely manual system, when the pressure returns to the programmed pressure, the other pumps may be increased to a level slightly below the level of the flow stream. However, this step may be made automatic by sensing the dip in pressure and starting to increase the pumping rate of other pumps at a time after the dip is sensed when the rate of change of pressure has stopped and the pressure of the primary liquid has increased to a level pressure at the programmed value of pressure.

Because each conduit from each pump is closed by a check valve when the pressure downstream of the check valve exceeds the upstream pressure, flowback from the pressurized main flow stream into the lower pressure conduits between the other pumps and the check valves upstream of them is avoided, thus reducing the danger of instability of the flow stream by the back flow from the primary pump. The check valves also prevent inadvertent mixing of the different solvents.

When the flow stream from the secondary pump is stabilized at the lower pressure, a pressure ramp is started to increase the pressure in the pressure control mode until the associated flow rate is established and then the second pump is switched to the flow rate control mode at that flow rate.

The offset of the ramp is established by sampling the pressure and holding it so that it is based on the starting pressure. The slope of the ramp is chosen to be as slow as is practical to prevent overshoot when the check valve opens but fast enough to match the pressures in a reasonable time compared to the extraction or analysis time. The time required is dependent on the accuracy or degree of matching between pressure transducers.

Once established, the pressure ramp if permitted to continue rising with this slope until equilibrium is reached at which time the check valve opens and the proper flow ratio (or composition) is established. Because the liquid from the pump is restrained by the pressure on the opposite side of the check valve with a pressure developed by the primary fluid, the pressure builds quickly to equilibrium at which time the check valve opens. This process is repeated for any other pumps in the system until liquid from each of the pumps is at the programmed pressure and composition. This means of pressure equilibration can also be used to match pressures of pumps for smooth changeover from one pump to the next in a continuous flow, controlled flow rate or controlled pressure system, of constant composition.

To achieve a higher degree of matching, the pressure transducers should be calibrated for the specific operating conditions. This calibration can be performed manually or automatically. In the above description of the pressure equilibration, after the check valve at the outlet of the secondary pump opens, the two pump pressures are known to match. At this point the pressure signals can be compared to provide a correction factor which is used in later equilibrations to match the transducer signals and thus shorten the equilibration time.

An alternate method of equilibrating the pressure and calibrating the transducer signals of a multiple pump system to match each other is to simultaneously deliver fluid from all pumps in the system until all check valves are open with fluid flowing. It can be determined when sufficient fluid to open the check valve has been pumped from each pump because the starting pressure, volume, and characteristics of the fluid in each pump are known. Until the check valve opens, the pump is compressing the fluid in a closed space. After the check valves open, all pumps are at the same pressure. At this point, the pressure signals can be compared to determine the correction factor or factors which will match the signals. The transducers may be calibrated at any time the check valves are known to be open with fluid flowing.

Still another method of equilibrating the pressures and calibrating the transducer signals of a multiple pump system to match is to connect temporarily the transducers by a common fluid path to force the pressures to match with a manual or automatic valve and opening it at the time it is desired to match the pressure signals. With matching pressures, the pressure correction factor is calculated.

Once all of the pumps have been brought on stream one by one to the controlled composition, the concentration and pressure of the liquid flowing into the column or extraction vessel are maintained at the programmed values by a feedback system. In a constant pressure mode of operation, a different flow rate control signal is developed for each pump to control the flow rate of that pump in proportion to the programmed concentration. These signals are obtained from a single feedback signal representing system pressure that is compared to a setpoint signal representing the programmed pressure to generate an error signal. This error signal is used to generate the different flow rate signals for each pump by multiplying it by a flow rate factor under the control of the gradient programmer.

In the preferred embodiment, the system pressure signal during the chromatographic or extraction run is determined from the transducers in each of the conduits between the outlets of the pumps and the check valve for the conduits although it could be obtained from a single transducer connected directly in line with the column or extraction vessel. However, transducers are used in each conduit associated with each pump between the pump's outlet and its check valve during the time period that the pumps are being brought on line and it is economical to use the same transducers rather than adding an additional transducer.

Any pressure transducer that is connected to the fluid mixer can be used to measure the system pressure. Therefore, any transducer whose associated check valve is open could accurately represent pressure. Because of the danger of that check valve closing at a low flow rate, it is preferable to use all available transducers to represent system pressure.

To use the transducers associated with each pump to generate a single system pressure, each signal from a transducer is multiplied by a factor representing the programmed percentage of the fluid in the conduit that the transducer is measuring and the multiplied signals are added to generate the system feedback pressure signal. In this manner, the feedback system permits control of both the pressure and the concentration of the liquid supplied to the column or extraction vessel with pressure transducers in the flow path that includes the pump outlet and the check valve for that pump.

From the above description, it can be understood that the fluid delivery system of this invention has several advantages, such as: (1) it is relatively inexpensive because it utilizes a minimum number of transducers of ordinary accuracy; (2) it provides stable pressure control and controlled composition of fluids; (3) it avoids backflow into a pump caused by mixing at high pressure; (4) it avoids stoppage of the flow by uneven pressure on the downstream side of check valves; (5) it permits differential pumping to control both rate of flow and composition of the mixed stream of fluids; and (6) it permits continuous flow from automatically refilling multiple syringe pumps without pressure or flow disturbance when switching from one pump to the next.

DESCRIPTION OF THE DRAWINGS

The above-noted and other features of the invention will be better understood from the following detailed description when considered in connection with the accompanying drawings, in which:

FIG. 3 is a block diagram of a typical unit for receiving and using the multiple fluids;

FIG. 4 is a block diagram of a pumping system used in the embodiment of FIG. 1;

FIG. 5 is a block diagram of another pumping system usable in the embodiment of FIG. 1;

FIG. 6 is a block diagram of a portion of the controller of FIG. 1;

FIG. 7 is a block diagram of another portion of the controller of FIG. 1;

DETAILED DESCRIPTION

Figure 1:
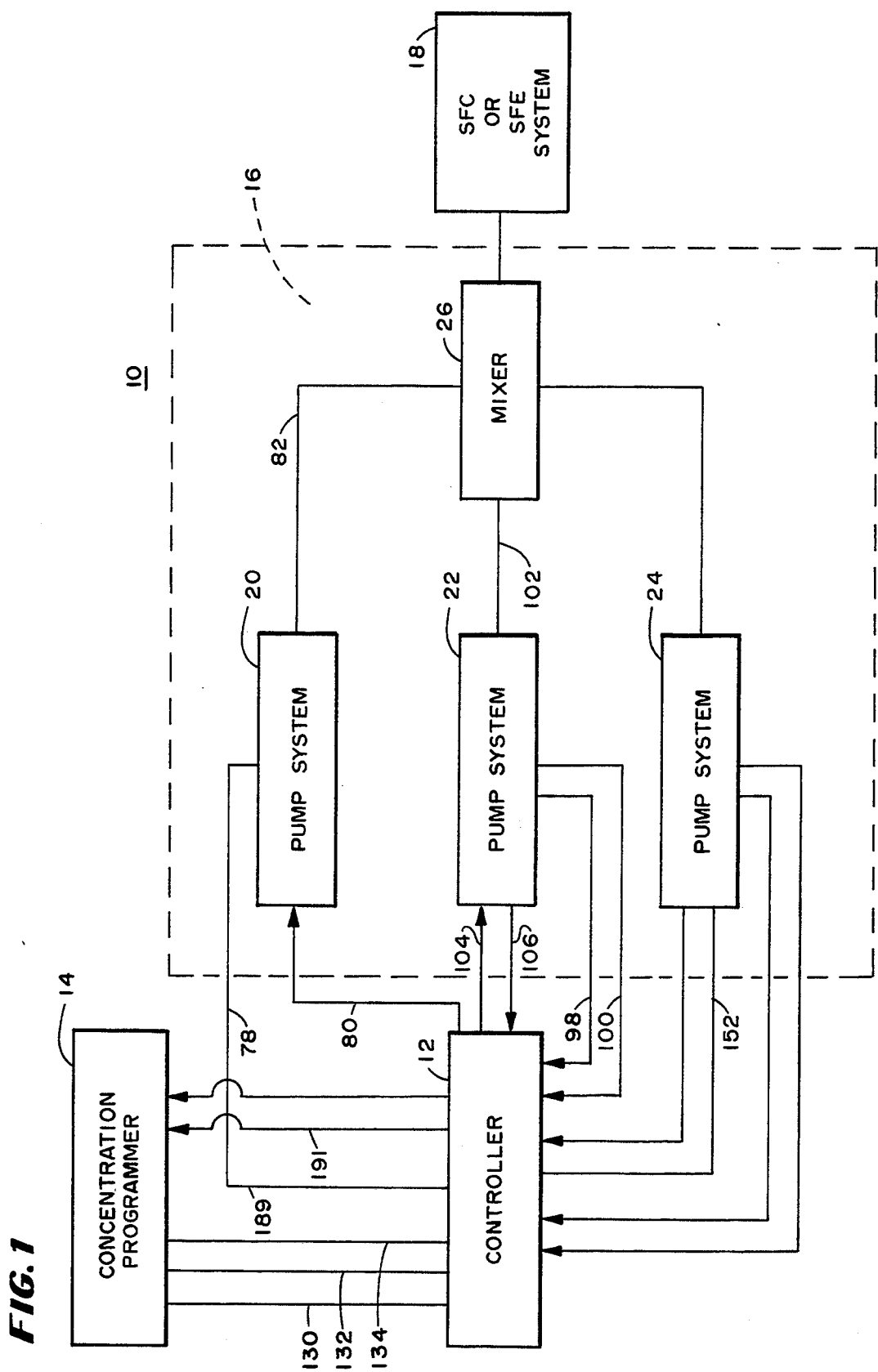
FIG. 1 is a block diagram of a multi-fluid supply system connected to a fluid receiving unit.

In FIG. 1, there is shown a block diagram of a separating system 10 having a controller 12, a concentration programmer 14, a fluid supply system 16, and a unit 18 that receives the mixture of fluids, which unit 18 may, for example, be a supercritical fluid chromatographic system or supercritical fluid extractor. The fluid delivery system including the concentration programmer 14, the controller 12, and the fluid supply system 16 are principally adapted to supply either a single fluid or a plurality of fluids to the receiving unit 18 while controlling the pressure and concentration of the components of the mixture.

The concentration programmer 14 supplies signals indicating the concentration of the individual components and is programmed to provide a change in components in the stream from the fluid supply system 16 at a controlled pressure. Suitable concentration programmers are known in the art and the concentration programmer 14 is not by itself a part of the invention except insofar as it cooperates as a gradient programmer with the controller 12 and fluid flow system 16. It is programmed to provide timed signals indicating the percentage composition, which in the preferred embodiment are digital although many analog gradient programmers are known. If an analog system is used, of course, a compatible interface will be necessary to connect it to the controller 12. Similarly, there are many supercritical flow extraction systems and chromatographic systems known in the art.

The fluid supply system 16 receives signals from the controller 12 which indicate the pumping rate to be utilized for each of the fluids being mixed, mixes the fluids and sends them to the unit 18. Signals are transmitted from the fluid supply system 16 to the controller 12 indicating any unequal pressure in lines from the individual fluids before they are mixed and the pressure in each line when it is in a steady condition. In this manner, the flow rates are maintained in proportion and at a pre-selected total amount even for compressible fluids while the pressure of the mixed flow stream is maintained constant.

The fluid supply system 16 includes first, second and third pumping systems 20, 22 and 24 and a mixer 26. Each of the pumping systems has an output line which communicates with the mixer 26, and the mixer 26 has an output line which communicates with the unit 18. The pumping systems 20, 22 and 24 receive electrical signals from the controller 12 to control the flow rate, and supply pressure signals from pressure transducers back to the controller 12. While three pumping systems are shown in FIG. 1 for explanation, any number of such systems may be used.

With this arrangement, the pumping systems 20, 22 and 24 are each controlled as to their flow rate so that the stable operating pressure into the mixer 26 beyond the pumping systems is controlled in such a way that one pump at a time is brought up to the operating pressure. The operating pressure, pump by pump, is sensed by changes in the pressure signal fed back to the controller 12.

Figure 2:
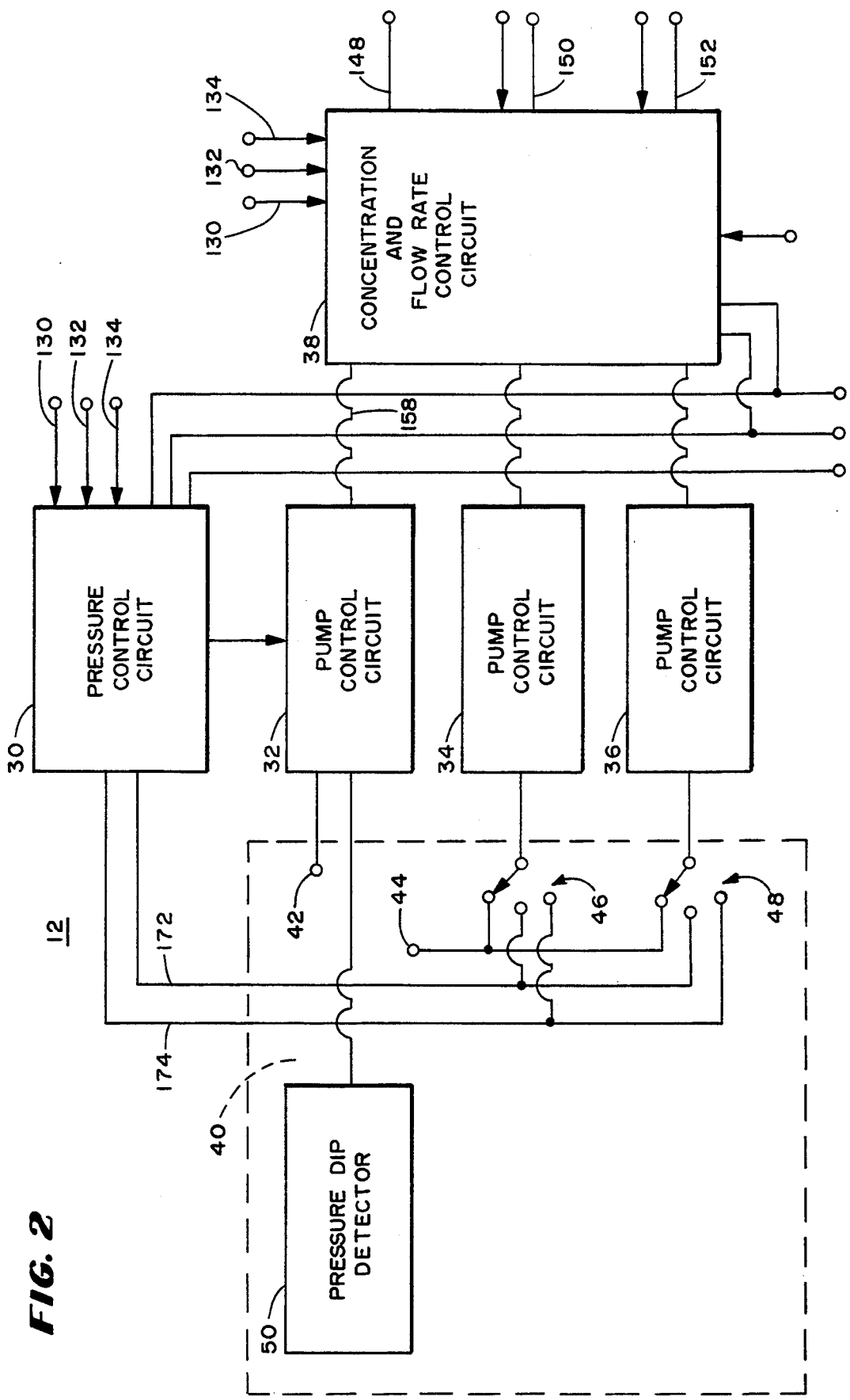
FIG. 2 is a block diagram of a controller used in the multiple fluid control system of FIG. 1.

In FIG. 2, there is shown a block diagram of the controller 12 having a pressure control circuit 30, first, second and third pump control circuits 32, 34 and 36, a concentration and flow rate control circuit 38 and a pressure and mode selection circuit 40. The concentration and flow rate control circuit 38 receives signals from the concentration programmer 14 (FIG. 1), from the pressure control circuit 30, and from the pump control circuits 32, 34 and 36 which signals are used to control the flow rate of the pumps. To control the flow rate, the concentration and flow rate control circuit 38 is also connected to the pumps to supply signals controlling the pumping rate and to receive feedback pressure signals.

The concentration and flow rate control circuit 38 may be adjusted either automatically such as under computer control or manually by switches: (1) to select certain pumps that are to operate independently of the other pumps or of pressure control; or (2) to ramp the pressure of the pumps at a fixed flow rate until they are pumping at the desired back pressure under constant flow rate conditions for stability purposes and to cause the pumps to be controlled by feedback related to final pressure and final concentration from the pump after the desired back pressure is reached.

The pressure mode selection circuit 40 is connected to the pump control circuits 32, 34 and 36 to select conditions such as pre-pressurized conditions or a back pressure that tracks the back pressure of a first master pump or to ramp to the pressure of a first pump. This pressure mode selection circuit 40 is able to connect any of these outputs and certain set point feedback signals to the pump control circuits 32, 34 and 36. For this purpose, the pressure and mode selection circuit 40 includes a pressure dip detector 50, a system pressure set point 42, an individual pump pressure set point 44, a first mode selection switch 46 and a second mode selection switch 48. In the preferred embodiment, pressure mode selection circuit 40 is implemented digitally.

The pressure dip detector 50 is electrically connected to receive changes in pressure from the pump control circuit 32 to receive sudden dips in pressure indicating the opening of the valve to the column or extraction vessel. This signal may be detected either on a meter or other instrument or automatically and used to determine the timing of institution of a fixed pressure ramp by additional pumps rather than the primary pump that initially pressurized the system. The mode selection switches 46 and 48 are respectively connected to pump control circuit 34 and pump control circuit 36 and are setable in either of three positions, which are: (1) a pre-pressurized position in which they are held at a low value of pressure; (2) a position in which they are connected to a signal representing a value lower than the pressure at the output of the master control pump as controlled by the pump control circuit 32 to track that pressure but at a lower pumping pressure; and (3) a position in which they are controlled by a pressure increase ramp used when the outlet pressure of the pump is being brought to system pressure.

In FIG. 3, there is shown a flow diagram of the fluid receiving unit 18 having an upstream valve 60, a supercritical fluid chromatographic system or supercritical fluid extraction system 62 and a downstream valve 64 with the supercritical fluid chromatographic system or supercritical fluid extraction system 62 communicating with both the upstream valve 60 and the downstream valve 64. The upstream valve 60 has its inlet port connected to the outlet port of the mixer 26 (FIG. 1) and its outlet port connected to the inlet port of the supercritical fluid chromatographic system or supercritical fluid extraction system 62.

With this arrangement, the pressure-controlled stream is blocked by the upstream valve 60 until the primary pump is pressurized, at which time it is opened, but the downstream valve 64 remains closed until the extraction vessel or the chromatographic column is also pressurized and then finally the downstream valve 64 is opened to permit the flow of the fluid to achieve separation within the system 62. After flow is established, any secondary pumps are brought up to pressure and mixing is begun.

The supercritical fluid extraction system may be the system disclosed in U.S. application Ser. No. 07/553,119 filed Jul. 13, 1990, and assigned to the same assignee as this application. The pumps may be the pumps disclosed therein and more specifically, the supercritical fluid extractor sold under the trademark SFX 2-10 manufactured by Isco, Inc., P.O. Box 5347, 4700 Superior Street, Lincoln, Nebr., 68504 U.S.A. and the 100D/260D syringe pumps sold by Isco, Inc., P.O. Box 5347, 4700 Superior Street, Lincoln, Nebr.

In FIG. 4, there is shown a fluid diagram of the pumping system 20 having a first pump 70, a fluid source 72, a pressure transducer 74, a check valve 76 and a conduit 82. The pump 70 is electrically connected to the controller 12 (FIG. 1) through conductor 80 to receive signals controlling its pumping rate and to the fluid source 72 containing a first or primary fluid that it pumps through the conduit 82. The pressure transducer 74 communicates with the fluid in the conduit 82 to measure the pressure of the fluid and applies a signal through conductor 78 representing this line pressure. The conduit 82 also communicates with the check valve 76 to permit flow through the outlet line 82 to the mixer 26 (FIG. 1) but to prevent flow from the line 82 back to the pump 70.

With this arrangement, the pressure transducer 74 provides an electrical signal as a feedback signal on conductor 78 back to the controller 12 (FIG. 1) and receives signals from the controller 12 through conductor 80 to control the amount of fluid pumped to the mixer 26 (FIG. 1). The feedback signal is used to closely control the pumping rate of the pump 70 so as to pressurize the system and form one component of the gradient applied through the valves to the supercritical fluid chromatograph or supercritical fluid extractor.

In FIG. 5, there is shown a flow diagram of the pumping system 22 having a pump 90, a fluid source 92, a pressure transducer 94, a check valve 96 and a conduit 102. This pumping system is identical to the pumping system 24 (FIG. 1) and only the pumping system 22 will be described. The pumping system 24 and any additional pumping systems that are to be controlled and contribute fluid to the mixer 26 (FIG. 1) are connected in the same manner and operate in a manner analogous to the pumping system 22.

In this system, the pump 90 receives a signal from the controller 12 (FIG. 1) on conductor 104 controlling the rate at which it pumps and provides a feedback signal on conductor 106 indicating the actual pumping rate to the controller 12. It supplies its fluid from the fluid source 92 through the conduit 102 that communicates with the pressure transducer 94 and the check valve 96 to the fluid source 92 for application to the mixer 26 (FIG. 1) in a manner similar to the manner that the fluid in conduit 82 (FIG. 4) communicates with the pressure transducer 74 and the check valve 76.

To supply information concerning the pressure in conduit 102, the pressure transducer 94 supplies signals through conductors 98 and 100 (FIG. 1) representative of the pressure in the line 102 to the controller 12 (FIG. 1) for use in the control of the pumping speed of the pump 90 to properly represent the amount of fluid from the fluid source 92 that is to be supplied to the mixer 26 (FIG. 1) to maintain the proper concentration of fluids and the proper pressure.

In FIG. 6, there is shown a block diagram of the concentration and flow rate control circuit 38 having first, second and third concentration multipliers 110, 112 and 114, first and second flow rate sample and hold circuits 116 and 118 and first and second flow rate input switches 120 and 122. The first flow rate input switch 120 controls the second pump and the second flow rate input switch 122 controls the third pump. In the preferred embodiment, the switches and concentration multipliers are implemented digitally.

To control the first, second and third pumps, the first concentration multiplier 110 is electrically connected to the conductor 148, the movable armature of the three-position first flow rate input switch 120 is electrically connected to conductor 150 and the movable armature of the second three-position flow rate input switch 122 is electrically connected to conductor 152. These conductors provide flow rate input signals to the pumping systems 20, 22 and 24 (FIG. 1) to control the pumping rate when the first flow rate input switch and the second flow rate input switch 120 and 122 respectively are connected to the first position to receive signals from the pump control circuits 34 and 36 respectively (FIG. 2) on conductors 156 and 154 respectively related to the pressure error between the measurement provided by their respective pressure transducers and pressure set points for the pre-pressure stage to be described hereinafter. This signal indicates the required flow rates to maintain the respective pressures with zero error.

In the second position of the switches, the armatures of switches 120 and 122 each receive a different ramping signal from the sample and hold circuits 116 and 118 respectively which ramping signal causes the corresponding one of the pumping systems 22 and 24 to ramp up to the final system pressure. In the third position, the armatures receive the flow rate from their respective one of the concentration multipliers 112 and 114 required to provide the programmed concentration. These signals will be described hereinafter.

When the movable armature of the three-position switches 120 and 122 are in their second position, the conductors 150 and 152 apply signals to their respective pumping system 22 and 24 (FIG. 1) equivalent to the pressure ramp pumping rates applied by the flow rate sample and hold circuits 116 and 118 which store those signals from output conductors 150 and 152 connected respectively to the pumping systems 22 and 24.

When the three-position switches 120 and 122 have their movable armatures connected to the third contact of the switch, the conductors 150 and 152 apply a signal from the concentration multipliers 112 and 114 respectively to control the pumping rate of the pumping systems 22 and 24 respectively. The concentration multipliers 112 and 114 are electrically connected to conductor 158 which is also connected to the concentration multiplier 110.

To provide signals for the separate pump flow rate, the conductor 158 is connected to the concentration multipliers 110, 112 and 114 to which it supplies the total flow rate signal necessary to maintain the programmed system pressure. This total flow rate signal sets the separate pump flow rates in conjunction with all three concentration multipliers to which it is connected. For this purpose the three concentration multipliers are also connected to receive their respective concentration signals on the corresponding one of the conductors 130, 132 and 134. Thus, the output signals from the three position switches when in the third position supply signals through conductor 148 to control the pumping system 20 (FIG. 1), conductor 150 to supply signals to the pumping system 22 and conductor 152 to supply signals to the pumping system 24.

The concentration multipliers 110, 112 and 114 calculate the signals to be applied to their output conductors and eventually to the respective pumps they control by multiplying signals on conductors 130, 132 and 134 respectively supplied by the concentration programmer 14 (FIG. 1) indicating the percentage of the final flow stream that is to be pumped by each of the pumping systems 20, 22 and 24 respectively. In this manner, each of the controllers supplies a signal controlling the respective pump so that it pumps a flow rate proportional to the fluid that is to be supplied to the mixer 26 (FIG. 1) representing its portion of the final flow stream to be supplied to the unit 18 (FIG. 1).

In FIG. 7, there is shown a block diagram of the pressure control circuit 30 having a pressure ramp generator 160, a pressure sample and hold circuit 162, a subtract circuit 164 and a system feedback pressure signal generator shown generally at 166. The system feedback pressure signal generator 166 receives signals on conductors 130, 132 and 134 from the concentration programmer 14 (FIG. 1) indicating the proportion of fluids to be supplied to the final mixture, and receives signals on conductors 78, 98 and 108 from the pressure transducers in the fluid from the first, second and third pumping systems 20, 22 and 24. From these signals, the system feedback pressure signal generator 166 generates and supplies a signal to conductor 170 as a system feedback signal to be compared to the reference pressure. This signal, together with the reference signal, ultimately will control the pressure of the fluid being applied to the unit 18 and will play a role in the preservation of the programmed concentration.

The subtract circuit 164 receives a signal on conductor 78 representing the pressure in the outlet line from the first pump 20, which is the primary fluid signal and subtracts a value which in the preferred embodiment is 300 pounds per square inch. It supplies a signal representing this reduced value to conductor 172 which controls the other pumps during a start-up phase while the system is being brought up to pressure in a manner to be described hereinafter.

This signal is supplied to the pressure sample and hold circuit 162 which samples and stores the signal and applies it to a pressure ramp generator 160. The pressure ramp generator 160 generates a constant rate ramp voltage during a second phase of the pressurization cycle so that during a first phase there is a pre-pressurization with a low value on all of the pumps except the first pump which is coming up to pressure, a second phase in which the signal on conductor 172 increases the pressure on the other pumps up to a value 300 pounds per square inch lower than the pressure on the first pump's outlet line and then a final phase in which a ramp voltage from the pressure ramp generator 160 is applied through a conductor 174 to bring the other pumps up to pressure.

To generate a signal representing system feedback for conductor 170, the system feedback pressure signal generator 166 includes a summing circuit 180, first, second and third pressure multipliers 182, 184 and 186 respectively, first and second detectors 188 and 190 respectively and first and second first derivative generators 192 and 194.

To control the initiation of the gradient program, the first and second detectors 188 and 190 detect the derivatives of the signals in conductors 98 and 108 connected to the second and third pressure transducers, which derivatives are generated by the first and second first derivative generators 192 and 194 electrically connected to conductors 98 and 108 respectively and to the detectors 188 and 190. The outputs of these generators are supplied to the detectors 188 and 190 respectively and they provide signals on conductors 189 and 191 respectively to the concentration programmer 14 (FIG. 1) indicating the opening of the check valves in the outlet conduits from the second and third pumping systems 22 and 24.

Any pressure transducer that is connected to the fluid mixer can be used to measure the system pressure. Therefore, any transducer whose associated check valve is open could accurately represent pressure. Because of the danger of that check valve closing at a low flow rate, it is preferable to use all available transducers to represent system pressure.

To use the transducers associated with each pump to generate a single system pressure, each signal from a transducer is multiplied by a factor representing the programmed percentage of the fluid in the conduit that the transducer is measuring and the multiplied signals are added to generate the system feedback pressure signal. In this manner, the feedback system permits control of both the pressure and the concentration of the liquid supplied to the column or extraction vessel with pressure transducers in the flow path that includes the pump outlet and the check valve for that pump.

For this purpose, the pressure multipliers 182, 184 and 186 receive the pressure signals from conductors 78, 98 and 108 representing pressure in the conduits from the first, second and third pumping systems 20, 22 and 24 and multiply these signals by the proportion of fluids programmed to be in the final stream as represented by signals on conductors 130, 132 and 134 applied to the multipliers 182, 184 and 186. The outputs from these multipliers are summed in the summing circuit 180 resulting in the output signal on conductor 170 representing a value of feedback pressure that contains within it a component related to the fluid as measured in the outlet lines from each of the pumping systems before they are applied and combined in the mixer 26 (FIG. 1).

In this manner, variations in any one of the outlet lines from any one of the pumps results in a corresponding representative change in the feedback signal 170 so that the pumping systems correct for the drop in pressure. This enables the system to control the pressure to the unit 18 (FIG. 1) without using a separate feedback transducer downstream of the mixer 26 (FIG. 1) and yet maintains the concentrations at the programmed value.

Figure 8:
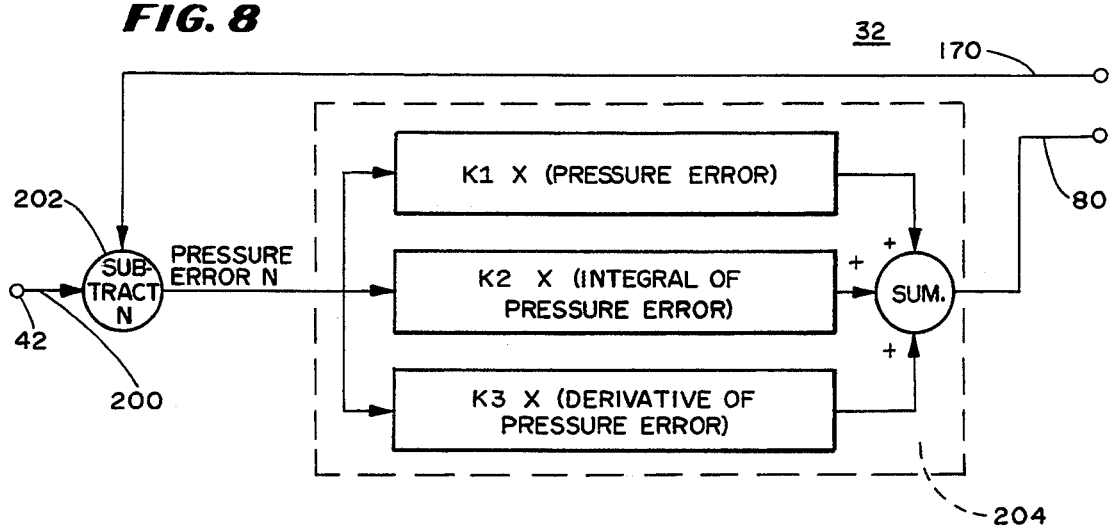
FIG. 8 is a block diagram of still another portion of the embodiment of FIG. 1.

In FIG. 8, there is shown a pump control circuit 32 having a comparator 202 and a feedback filter 204. The comparator 202: (1) receives a signal representing system feedback on conductor 170 from the summing circuit 180 (FIG. 7) in the system feedback pressure signal generator 166 (FIG. 7); (2) receives a signal representing the set pressure voltage on conductor 200 from the pressure system voltage at 42; (3) compares the two signals; and (4) generates an error signal representing the difference between the two signals.

The error signal from the comparator 202 is applied through the filter 204, which is for a second-degree feedback circuit, to conductor 80 for application to the pump system 20 (FIG. 1). This is one of three pump control circuits, 32, 34 and 36 (FIG. 2) each of which receives a feedback signal. The pump control circuit 32 receives the system pressure signal on conductor 170 and the pump control circuits 34 and 36 (FIGS. 2) each receive a corresponding signal from the corresponding pressure transducer in the corresponding conduit with which it is associated and transmits its corresponding feedback signal to its corresponding one of the pumping systems.

The pump control circuits 34 and 36 (FIG. 2) transmit their feedback signals through selector switches 46 and 48. The comparison feedback signal is received from switches 46 and 48 so that it receives in one position the pre-pressure potential, in another position the difference between the measured pressure from the transducer in the first conduit 82 (FIGS. 1 and 4) minus 300 pounds per square inch and in the final position receives the ramp potential on conductor 174 from the pressure ramp generator 160 (FIG. 7).

Figure 9:
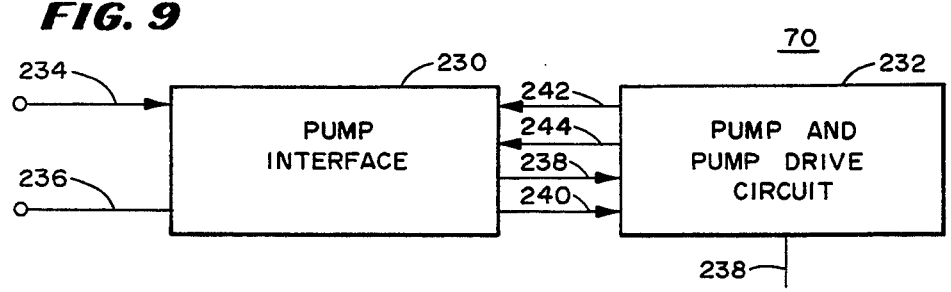
FIG. 9 is a block diagram of a pump usable in the embodiment of FIG. 1.

In FIG. 9, there is shown a block diagram of the pump 70 having a pump interface 230 and a pump and pump drive circuit 232. The pump interface 230 receives a signal on conductor 234 indicating the programmed flow rate and provides an outlet signal on conductor 236 indicating the actual flow rate from the pump 70.

The pump interface 230 transmits signals to the pump and pump drive circuit 232 indicating the position to which the rotary pump motor is to move to provide position control over the drive of the pump. Fluid is pumped in response to that signal through a conduit 238. The drive signal to cause the pump to pump liquid is applied to the pump and pump drive circuit 232 by the pump interface 230 through conductor 238.

To match the pump drive supply voltage to the motor speed, a signal is applied through conductor 240 when the required speed increases above a threshold value. This signal increases the voltage to the pump and pump drive circuit 232. As the pump pumps liquid through the conduit 238 under the control of the pump and pump drive circuit 232, the movement of the rotary motor of the pump results in changing position feedback signals on conductors 242 and 244 indicating the position of the motor to the pump interface 230 which compares it to the programmed position for the programmed amount of liquid to be pumped and adjusts the power to a power amplifier that applies power to the pump motor to control the pumped liquid to follow the programmed flow rate.

Figure 10:
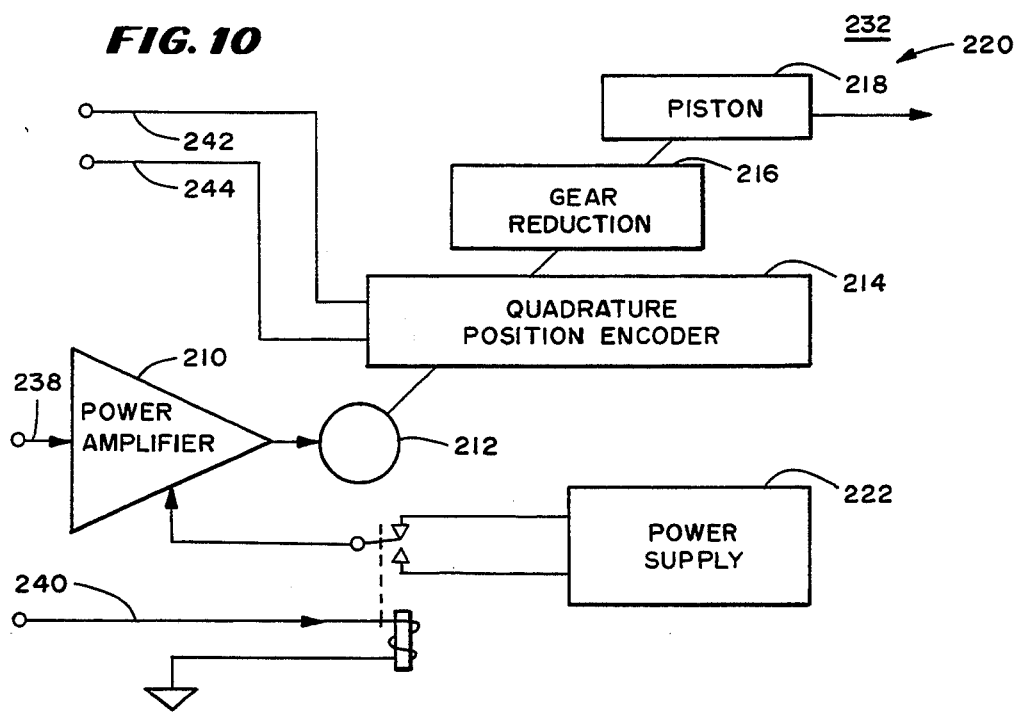
FIG. 10 is a schematic diagram of a portion of the pump of FIG. 9.

In FIG. 10, there is shown a pump and pump drive circuit 232 having a power amplifier 210, a motor 212, a quadrature position encoder 214, a gear reduction 216, a piston 218 and a cylinder 220. The power amplifier 210 receives signals on conductor 238 and uses them to energize the motor 212. The motor 212 drives the piston 218 into the cylinder 220 to pump liquid.

The quadrature position encoder 214 develops signals which it transmits on conductors 242 and 244 to the pump interface 230 (FIG. 9) as a position feedback signal. The pump interface 230 (FIG. 9) compares this signal to the input position signal and develops an error signal which is utilized to maintain the pump at the programmed speed. The gear reduction 216 connects the D.C. motor 212 to the piston 218 and includes a transmission of any conventional form to transmit the motion with increased force and a ball screw linear actuator to drive the piston.

The power amplifier 210 operates in two regions determined by the voltage applied to it by the power supply 222. In one region the power supply 222 provides it with 40 volts and in the other region it is supplied by the power supply 222 with 80 volts. The bias voltage is connected to a two-position switch 224 controlled by a relay 248 in response to a signal from the pump interface 230 indicating that the motor speed is going from one region to another.

Figure 11:
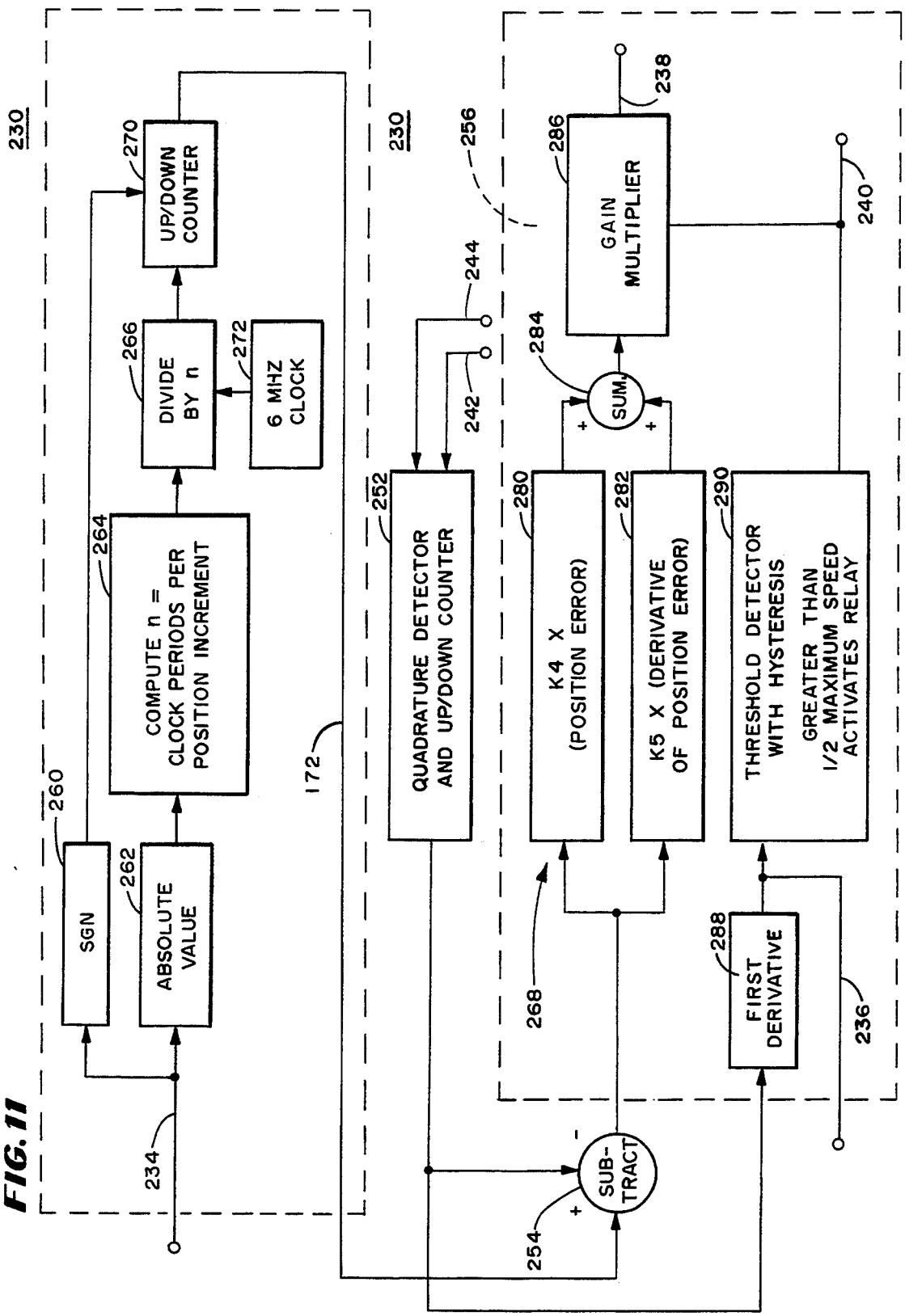
FIG. 11 is a block diagram of a pump control system usable in the embodiment of FIG. 9.

In FIG. 11, there is shown a block diagram of the pump interface 230 having a motor position set point circuit 250, a quadrature detector and up/down counter 252, a comparator 254 and a motor position control input signal circuit 256. These circuits are connected together to receive information concerning the pumping rate and provide signals that control the pump and pump drive circuit 232 (FIG. 9) in response thereto.

To determine the power that must be applied to the pump motor 212 (FIG. 10) to drive the pump piston 218 (FIG. 10) at the proper speed for the desired flow rate, the motor position set point circuit 250 receives a signal indicating the programmed flow rate on conductor 234 and calculates the motor angular position set point from it. This value is applied to the comparator 254. The quadrature detector and up/down counter 252 receives signals indicating the measured motor position from the quadrature position encoder 214 (FIG. 10) on conductors 242 and 244 and applies a signal indicating that position to the comparator 254, which compares the programmed set point with the position of the pump and provides a position error to the motor position control circuit 256.

To control the power applied to the motor 212 (FIG. 10) the motor position control circuit 256: (1) receives a position error from comparator 254; (2) receives the output from the quadrature detector and up/down counter 252; and (3) provides the gain signal on conductor 238 to the power amplifier 210 (FIG. 10) and a signal on conductor 240 to control the relay 248 (FIG. 10).

To calculate the motor position set point, the motor position set point circuit 250 includes a means for developing a signal indicating the programmed direction for flow 260, a means for developing a signal indicating the absolute value of flow 262, a means for determining the number of clock periods per position increment 264, a clock pulse generator 272, a divider 266 and an up/down counter 270. The flow rate input signal on conductor 234 results in a signal indicating the direction of flow, and this signal is applied to the up/down counter 270 to determine whether the pulses should be counted up or down to result in the motor angular position set point on conductor 172. The absolute value from the flow rate input on conductor 234 is determined in terms of position increment rate and digitally applied to the means for calculating the clock periods per position increment 264.

To calculate the clock periods per position increment, the inverse of the flow rate magnitude such as the number of minutes per liter of flow is multiplied by the number of clock periods per minute supplied by the clock 272 and the product of this multiplication is multiplied by the number of liters of liquid pumped per position increment of the pump. In the preferred embodiment, the calculations are made on digital signals by a computer program, but circuitry such as that shown in the blocks could be used. The clock divider consists of two stages of which the first is hardware and the second computational.

Instead of a hardware multiplier, a computer program is used in the preferred embodiment, but hardware multipliers, dividers and up/down counters are known in the prior art and could be used instead. The computer used in the preferred embodiment is an Intel 80106KB-12 microprocessor manufactured and sold by Intel Corporation, 3065 Bowers Avenue, Santa Clara, Cal. 95051. (Intel is a trademark of Intel Corporation. The module used to implement the operation related to this invention is attached hereto as appendix A.

To determine the motor angular position setpoint from the clock periods per position increment 264, the output from a clock pulse generator 272, which in the preferred embodiment is a six megahertz clock, is divided by the output of the computer 264 representing the clock periods per position increment supplied to a divider 266 to divide the output of the six megahertz clock 272 by the number of clock periods per position increment 264. This signal is totaled by up/down computer 270 and supplied to the comparator 254.

To develop a signal indicating the motor angular position feedback for the motor 212 (FIG. 10), a conventional quadrature detector and up/down counter 252 receives signals on conductors 242 and 244 and converts them to the motor angular position feedback for application to the comparator 254.

To generate a signal indicating the motor drive input, the motor position control circuit 256 includes a feedback circuit 268, a gain multiplier 286, a threshold detector 290 and a first derivative generator 288. The feedback circuit 268 is connected to the comparator 254 to receive an error signal and is connected to the gain multiplier 286 so that the gain multiplier 286 provides a signal 238 for application to the power amplifier 210 (FIG. 10). The gain multiplier 286 is electrically connected to the output of the threshold detector 290 to change the region or level of gain depending on whether the conductor 240 applies a signal on conductor 240 to increase the bias of the power amplifier 210 or decrease it as described in connection with FIG. 10. This keeps the overall loop gain constant.

The first derivative generator 288 has its input electrically connected to the output of the quadrature detector and up/down counter 252 to receive a pulse count indicating the angular position of the motor 212 (FIG. 10) and to generate a signal indicating the flow rate therefrom. This signal is applied to conductor 236 as a feedback signal and to the threshold detector 290. The threshold detector 290 provides a signal to conductor 240 when its threshold is exceeded, and its threshold in the preferred embodiment is set to be larger than one-half the maximum speed of the motor 212.

In operation, the primary fluid is first pumped by the primary pumping system 20 (FIG. 1) to pressurize the system at start up while both valves 60 and 64 (FIG. 3) communicating with the inlet and outlet ports of the column or extraction vessel are closed. If only one fluid is to be used, the valve 60 (FIG. 3) may be opened at the time the desired pressure is reached followed by the valve 64 (FIG. 3) after the system is pressurized and the pump speed controlled thereafter to maintain that pressure. The pump may be controlled by a feedback circuit from a pressure transducer 74 (FIG. 4) in the flow stream that measures the pressure at which the fluid is being delivered.

When a plurality of different fluids are being pumped into the mixer 26 (FIG. 1) to form the final composition of fluids, the system is pressurized first with the primary fluid while the valve 60 (FIG. 3) to the column or extraction vessel is closed. The valve 60 to the column or extraction vessel is then opened and the system repressurized with the primary fluid. The valve 64 (FIG. 3) to the column or extraction vessel outlet is opened manually in some embodiments and automatically in others. For automatic opening, stabilization of the pressure is sensed when the magnitude of the pressure error is less than five psi. For manual operation, the detector may be a lamp or other annunciator. In the preferred embodiment, this function is performed by a computer control system that detects the signal as described above in connection with FIG. 1.

When the valve 60 (FIG. 3) to the pressure vessel or chromatographic column or other receiving unit 18 (FIGS. 1 or 3) is opened, a dip in pressure may be sensed in the fluid path through which the primary fluid is flowing. This instability is cured by controlling the pump speed of the primary pump before other pumps begin increasing their pressure. In a completely manual system, when the pressure returns to the programmed pressure, the other pumps may be increased to a level slightly below the level of the flow stream. However, this step may be made automatic by sensing the dip in pressure and starting to increase the pumping rate of other pumps at a time after the dip is sensed when the pressure of the primary liquid has increased to a level pressure at the programmed value of pressure.

Because each conduit from each pump is closed by a different one of the check valves such as 76 (FIG. 4) and 96 (FIG. 5) when the pressure downstream of the check valve exceeds the upstream pressure, flowback from the pressurized main flow stream into the lower pressure conduits between the other pumps and the check valves upstream of them is avoided, thus reducing the danger of instability of the flow stream by the back flow from the primary pump.

When the flow stream from the secondary pump is stabilized at the lower pressure, the valve 64 (FIG. 3) is opened to cause fluid to flow through the supercritical system, and after flow is stable, a pressure ramp is started to increase the pressure until the primary and secondary pump pressures match.

The offset or starting pressure of the ramp is established by sampling the primary pressure and holding it. The slope of the ramp is chosen to be as slow as is practical to prevent overshoot when the check valve opens but fast enough to match the pressures in a reasonable time compared to the extraction or analysis time. The time required is dependent on the accuracy or degree of matching between pressure transducers. If for example the transducers are matched to within five psi (pounds per square inch), the pressure ramp could rise by ten psi instead of 300 psi, resulting in much shorter equilibration time.

Once established, the pressure ramp is permitted to continue rising with this slope until equilibrium is reached at which time the check valve opens and the proper flow ratio (or composition) is established. Because the liquid from the pump is restrained by the pressure on the opposite side of the check valve with a pressure developed by the primary fluid, the pressure builds quickly to equilibrium at which time the check valve opens. This process is repeated for any other pumps in the system until liquid from each of the pumps is at the programmed pressure and composition. This means of pressure equilibration can also be used to match pressures of pumps for smooth changeover from one pump to the next in a continuous flow, controlled flow rate or controlled pressure system, of constant composition.

The ramp may be started under a pressure control mode and later continued by a flow control mode. The reason for switching of modes is that the pressure ramp is smoother in the constant flow rate mode which allows a more reliable detection of check valve opening. Once the pressure ramp has started under pressure control, it continues with the programmed slope until the flow rate which produces the desired ramp rate has been measured. The pump then switches to constant flow mode at this measured flow rate and continues the ramp until equilibrium is reached at which time the check valve opens and the proper flow ratio (or composition) is established.

Because the liquid from the pump is restrained by the pressure on the opposite side of the check valve with a pressure developed by the primary fluid, the pressure builds quickly to equilibrium at which time the check valve opens. The check valve opening is indicated by a flattening of the pressure ramp when the piston begins pumping into the controlled pressure system instead of the sealed pump cylinder. This ramp rate change is sensed by first derivative generator 192 and detector 188 (FIG. 7). This process is repeated for any other pumps in the system until liquid from each of the pumps is at the programmed pressure.

To achieve a higher degree of matching, the pressure transducers should be calibrated for the specific operating conditions. This calibration can be performed manually or automatically. In the above description of the pressure equilibration, after the check valve at the outlet of the secondary pump opens, the two pump pressures are known to match. At this point the pressure signals can be compared to provide a correction factor which is used in later equilibrations to match the transducer signals and thus shorten the equilibration time.

An alternate method of equilibrating the pressure and calibrating the transducer signals of a multiple pump system to match each other is to simultaneously deliver fluid from all pumps in the system until all check valves are open with fluid flowing. It can be determined when sufficient fluid to open the check valve has been pumped from each pump because the starting pressure, volume, and characteristics of the fluid in each pump are known. Until the check valve opens, the pump is compressing the fluid in a closed space.

After the check valves open, all pumps are at the same pressure. At this point, the pressure signals can be compared to determine the correction factor or factors which will match the signals. The transducers may be calibrated at any time the check valves are known to be open with fluid flowing. This method may not be optimum in cases where the pumps are pumping different fluids and the initial composition of the solvent mixture must be known at all times.

Figure 12:
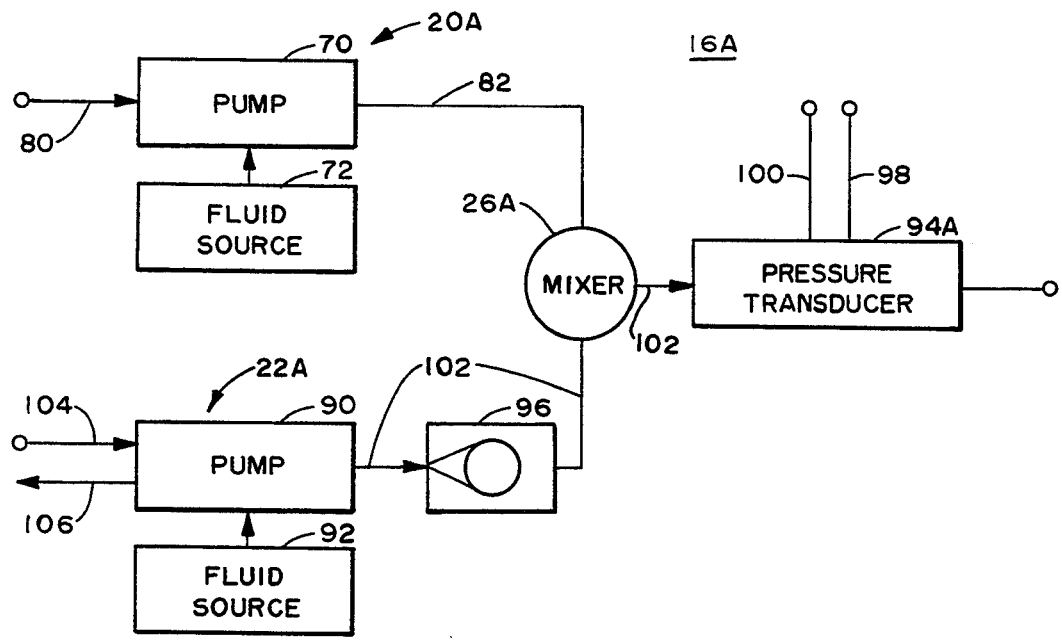
FIG. 12 is a schematic flow diagram of another embodiment of fluid flow system useful in the multifluid supply system of FIG. 1.

In FIG. 12, there is shown another embodiment of fluid flow system 16A having pumps 70 ad 90, fluid sources 72 and 92, valve 96, mixer 26A and pressure transducer 94A. In this embodiment, a plurality of pumps such as 70 and 90 can be equalized in pressure with a single pressure transducer 94 in the system if such transducer is connected on the downstream side of the back flow preventing check valves as shown in FIG. 12. The primary solvent pump 70 which is pressurized first, does not require a check valve. The secondary and other pumps such as 90 have an outlet check valve such as 96 connected in series with the fluid path.

Operation is begun by pressurizing the primary pump 70 with the secondary pump 90 at a low pressure, thus closing the secondary pump outlet check valve 96 by pressure differential. The secondary pump pressure is then ramped to match the primary pump pressure in the manner described in the preceding paragraph.

When the pressure matches, the check valve 96 opens, releasing additional fluid flow into the mixer outlet. The increased flow results in a pressure fluctuation that is detectable by comparing the pressure to a value sampled before the perturbation or by detecting changes in the first or successive derivatives of pressure. This process is repeated for any other pumps in the system until all pumps are delivering at the programmed pressure, flow or composition.

Figure 13:
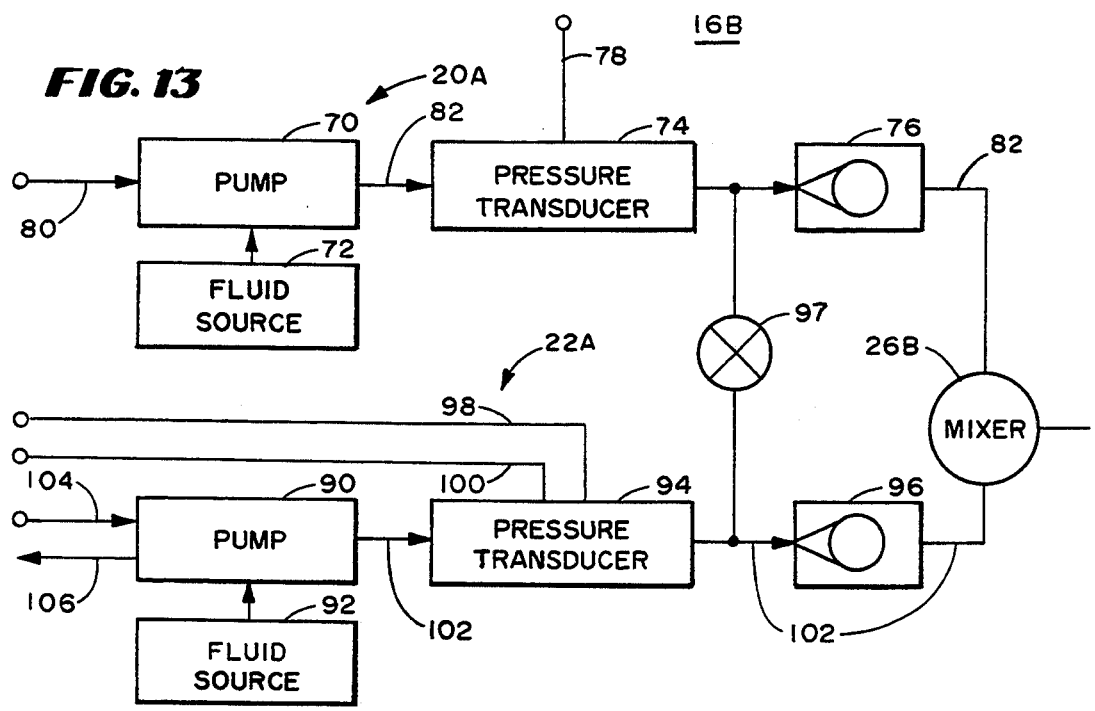
FIG. 13 is a schematic flow diagram of still another embodiment of fluid flow system useful in the multifluid supply system of FIG. 1.

In FIG. 13, there is shown still another fluid flow system 16B for equilibrating the pressures and calibrating the transducer signals of a multiple pump system having having pumps 70 ad 90, fluid sources 72 and 92, valve 96, mixer 26A and pressure transducers 74 and 94, valve 97 and mixer 26. In this embodiment, a plurality of transducer such as 74 and 904 can be matched by connecting temporarily the transducers by a common fluid path through valve 97 to force the pressures to match. The manual or automatic valve 97 is placed in a fluid path between the transducers and opened at the time it is desired to match the pressure signals.

With or without fluid flowing, the pressures will match, at which time the pressure correction factor is calculated. The valve or valves are closed to allow variable ratios, or on the other hand, continuous flow of the fluids to be delivered. The transducer may be calibrated by opening the connecting valve at any time when it is acceptable to do so. This method may not be optimum if for some reason it is unacceptable to allow any solvent flow from one pump to the other when the valve is opened.

Once all of the pumps have been brought on stream one by one to the controlled composition, the concentration and pressure of the liquid flowing into the column or extraction vessel are maintained at the programmed values by a feedback system. In a constant pressure mode of operation, a different flow rate control signal is developed for each pump to control the flow rate of that pump in proportion to the programmed concentration. These signals are obtained from a single feedback signal representing system pressure that is compared to a setpoint signal representing the programmed pressure to generate an error signal. This error signal is used to generate the different flow rate signals for each pump by multiplying it by a flow rate factor under the control of the gradient programmer.

In the preferred embodiment, the system pressure signal during the chromatographic or extraction run is determined from the transducers in each of the conduits between the outlets of the pumps and the check valve for that conduit although it could be obtained from a single transducer connected directly in line with the column or extraction vessel. However, transducers are used in each conduit associated with each pump between that pump's outlet and its check valve during the time period that the pumps are being brought on line and it is economical to use the same transducers rather than adding an additional transducer.

To use the transducers associated with each pump to generate a single system pressure, each signal from a transducer is multiplied by a factor representing the programmed percentage of the fluid in the conduit the transducer is measuring and the multiplied signals are added to generate the system feedback pressure signal. In this manner, the feedback system permits control of both the pressure and the concentration of the liquid supplied to the column or extraction vessel with pressure transducers in the flow path that includes the pump outlet and the check valve for that pump.

From the above description, it can be understood that the multiple solvent delivery system of this invention has several advantages, such as: (1) it is relatively inexpensive because it utilizes a minimum number of transducers to supply control feedback for several pumps and also to control the pressure of a final mixed stream; (2) it provides both stable pressure control of the mixture of fluids and also control over the composition of the fluids; (3) it avoids backflow into a pump caused by mixing at high pressure; (4) it avoids stoppage of the flow by uneven pressure on the down side of check valves; and (5) it permits differential pumping to control both rate of flow and composition of the mixed stream of fluids.

While a preferred embodiment of the invention has been described with some particularity, many modifications and variations in the system are possible within the light of the above teachings. It is therefore to be understood that, within the scope of the appended claims, the invention may be practiced other than as specifically described.

```
/********************/
/*    M_PUMP.C      */
/*    MULTI_PUMP    */
/********************/
#include <xternal.h>
include <NEWKEY.H> extern void update_time_BM();
extern long get_volM();
extern int abs1();
```

```c
/*********************/
/* external variables    */
/*********************/
extern unsigned char sfx_flag;
extern unsigned char mbefore, mbeforeB;
extern unsigned char pump_type, pump_typeB, flowsum, multi_pump;
extern unsigned char display_pump, access_out, valve_type;
extern char pump_cycle;
extern char mode,modeB,status,statusB;
extern int flow_avg, flow_avgB;      /* LITERS/MIN * 1E5 */
extern int pdmaxB;
extern int Kg, last_Kg, temp_Kg;
extern unsigned press_set, press_setB, poffset, poffsetB;
extern unsigned int min_mod_press;
extern long prev_val, max_refill, max_refillB;
extern long max_vol, max_volB, refill_mark;
extern unsigned long flowset_cf;

unsigned press_der();

unsigned int samp_press;

update_multi_pumpM()
  {
  unsigned int pressin_temp;

if (status= =stop && statusB= =stop)
    {
    pump_cycle=0;
    modeB=mbeforeB;
    Kg=poffset-poffsetB;
    if (FLOWSETR= =100L)
      {
      FLOWSETR=max_refill*10000L;
      FLOWSETRB=max_refillB*10000L;
      }
    FLOWSET=flowset_cf;
    PRESSIN=press_set+poffset;
    }
if (multi_pump= =modifier)
  {
  if (modeB!=refill && (status= =stop || mode= =refill))
    {
    if ((long)PRESSB-(long)poffsetB > (long)PRESS-(long)poffset-1500 &&
      (long)PRESS-(long)poffset > 1550)
      {
      CNTRLB| =0x6;       /* put pump B in const press */
      modeB=const_press;

pressin_temp=PRESS-poffset;
    if (pressin_temp > 1750)   /* if A pressure is > 350 */
      pressin_temp=min_mod_press+poffsetB;
    else if (pressin_temp > 1550) /* if A pressure is > 310 */
      pressin_temp=(PRESS-poffset+poffsetB-1500);  /* =psi*5 */
    else
```

```
    pressin_temp = 50 + poffsetB;
PRESSINB = pressin_temp;
PINTGB = 0;
CNTRLB| = 0x1; statusB = run;   /* set pump B to run */
}
else if (abs1(PRESERRB) < = 10 || (long)PRESSB - (long)poffsetB < 50)
CNTRLB& = 0xfe; statusB = stop;  /* set pump B to stop */
}
else if (mode = = const_press)
{
if (pump_cycle = = 0 && status! = stop)
{
flowsum = 1;        /* add sum of A & B flowrate */
if (FLOWOUTB = = 0)
  {
  CNTRLB| = 0x6;      /* put pump B in const press */
  modeB = const_press;
  }
pressin_temp = PRESS-poffset;
if (pressin_temp > 1750)    /* if A pressure is > 350 */
   pressin_temp = min_mod_press + poffsetB;
else if (pressin_temp > 1550) /* if A pressure is > 310 */
   pressin_temp = (PRESS-poffset + poffsetB-1500);  /* =psi*5 */
else
     pressin_temp = 50 + poffsetB;
   PRESSINB = pressin_temp;
   PINTGB = 0;
   CNTRLB| = 0x1; statusB = run;   /* set pump B to run */ if (status = = run && abs1(PRESERR) < = 25)
     status = hold;
   if (status = = hold && PRESERR > = 1250)
     status = equil;
   if (status = = equil && abs1(PRESERR) < = 25)
     pump_cycle = 1;
}
if (pump_cycle = = 1)      /* goto pressB = pressA-300 */
{
pressin_temp = (PRESS-poffset + poffsetB-1500);  /* psi*5 */
if ((long)pressin_temp-(long)poffsetB < 50)
   pressin_temp = 50 + poffsetB;
PRESSINB = pressin_temp;
if (FLOWOUTB = = 0 && statusB = = stop)
   {
   CNTRLB| = 0x6;    /* put pump B in const press */
   modeB = const_press;
   PINTGB = 0;
   CNTRLB| = 0x1; statusB = run;  /* set pump B to run */
   }
if (abs1(PRESERR) < = 10 && abs1(PRESERRB) < = 10 && statusB = = run)
   {
   /* FLOWSETB = 5000000L; */
      update_time_BM(1);       /* reset clock B */
   prev_val = PRESSINB;
   TEMPTIME = 15000;
```

```
    pump_cycle=2;
    }
}
if (pump_cycle==2)        /* pressure ramp */
{
PRESSINB=REALTIMEB/60L+prev_val;
if (!TEMPTIME)
   {
   PRESDERB=pdmaxB=0;
   FLOWSETB=flow_avgB*100000L;
   CNTRLB&=0xfb;     /* put pump B in const flow */
   TEMPTIME=1000;
   pump_cycle=3;
   }
}
if (PRESDERB > pdmaxB)
pdmaxB=PRESDERB;
if (pump_cycle==3 && !TEMPTIME)
{
if (PRESSB-poffsetB > PRESS-poffset+2500) /* check for overshoot */
   {
   CNTRLB&=0xfe; statusB=stop; /* set pump B to stop */
   pump_cycle=1;
   }
if (pump_cycle==3 && PRESDERB < 1 && pdmaxB > 7)
   {
   Kg=PRESS-PRESSB;
   CNTRLB|=0x6;      /* put pump B in const press */
   /* set bit 6 high for grad mode */
   CNTRL|=0x40;
   CNTRLB|=0x40;
   TEMPTIME=10000;
   pump_cycle=4;
   status=run;
   }
}
if (pump_cycle==4)
{
if (!TEMPTIME)
   {
   ACOUNT=0;
   BCOUNT=0;
   TEMPTIME=10000;
   }
if (ACOUNT==128)
   {
   ACOUNT=129;
   BCOUNT=129;
   Kg=PRESSAVG-PRESSAVGB;  /* Kg=difference+poffset-poffsetB */
   TEMPTIME=20000;
   }
if (abs1(PRESERR)>250)
   {
   CNTRLB&=0xfe; statusB=stop; /* set pump B to stop */
   /* set bit 6 low to clear grad mode */
   CNTRL&=0xbf;
```

```
    CNTRLB& = 0xbf;
    status = equil;
    pump_cycle = 1;
    }
  }
 if ((mode = = const_flow && multi_pump = = con_flow_cf) ||
    (mode = = const_press && multi_pump = = con_flow_cp))
  {
   if (pump_cycle = = 0 && status = = rapid)
     {
     access_out& = 0x4F; access_out| = 0x40;  /* set digital output
                           on a & b */
     ACCESS = access_out;              /* open outlet on pump A */
     pressin_temp = (PRESS-Kg-1500); /* psi*5 */
     if ((long)pressin_temp-(long)poffsetB < 50)
        pressin_temp = 50 + poffsetB;
     PRESSINB = pressin_temp;
     CNTRLB| = 0x6;    /* put pump B in const press */
     CNTRLB| = 0x1; statusB = run;  /* set pump B to run */
     modeB = const_press;
     }
   if (pump_cycle = = 100 && status = = run)  /* pump_cycle is set in rapid */
     {          /* after rapid: pump B is match before going on */
     PRESSINB = PRESS-Kg;
     if (PRESERRB < 25 && !TEMPTIME)   /* within 5 psi */
        pump_cycle = 0;
     }
   if (pump_cycle = = 0 && status = = run)
     {
     if (mode = = const_flow)
       {
       CNTRL& = 0xfb;           /* pump A in const flow */
       CNTRLB& = 0xfb;          /* pump B in const flow */
       FLOWSET = FLOWSETB = (flowset_cf/2);   /* both pump at 1/2 flowset */
       modeB = const_flow;
       status = statusB = equil;
       }
     if (mode = = const_press)
       {
       PRESSIN = press_set + poffset;
       PRESSINB = press_set + poffsetB;
       CNTRL| = 0x6;    /* put pump A in const press */
       CNTRLB| = 0x6;   /* put pump B in const press */
       CNTRL& = 0xbf;   /* reset grad mode */
       CNTRLB& = 0xbf;  /* reset grad mode */
       modeB = const_press;
       statusB = run;
       if (PRESERR < 250 && PRESERRB < 250)   /* if within 50 psi */
         {
         CONCEN = 25000;  /* both pump at 1/2 (50%) speed */
         PINTG = PINTG + PINTGB;
         CNTRL| = 0x40;    /* set bit 6 high for grad mode */
         CNTRLB| = 0x40;   /* set bit 6 high for grad mode */
         status = statusB = equil;
         Kg = poffset-poffsetB;
```

```
     last_Kg=0xA5A5;
    }
  }
  CNTRL| =0x1;    /* set pump A to run */
  CNTRLB| =0x1;   /* set pump B to run */
  flowsum=1;      /* add sum of A & B flowrate */
  press_der(0);
  access_out&=0x5F; access_out|=0x50; /* set digital output on a & b */
  ACCESS=access_out;              /* open outlet on pump A & B */
  display_pump=a_pump;
  }
if (pump_cycle= =0 && status= =equil)
  {
  if (mode= =const_flow)
  FLOWSET=FLOWSETB=(flowset_cf/2);   /* both pump at 1/2 flowset */
  if (press_der(2))
  {
  status=statusB=run;
  TEMPTIME=20000;
    if(get_volM(POSITIONB,pump_typeB)>get_volM(POSITION,pump_type))
    pump_cycle=8;
  else
    pump_cycle=1;
  }
  }
if (pump_cycle!=0 && status= =run)
  {
  if (pump_cycle= =1)    /* measure & adjust B matching factor */
  {
  display_pump=a_pump;
  if (mode= =const_flow)
    {
    FLOWSET=FLOWSETB=(flowset_cf/2);   /* both pump at 1/2 flowset */
    }
  if (!TEMPTIME)
    {
    ACOUNT=0;
    BCOUNT=0;
    TEMPTIME=10000;
    }
  if (ACOUNT= =128)
    {
    ACOUNT=129;
    BCOUNT=129;
    temp_Kg=PRESSAVG-PRESSAVGB; /* Kg=difference +
                                                  poffset-poffsetB */
    TEMPTIME=2500;
    pump_cycle=2;
    }
  }
  if (pump_cycle= =2)          /* ramp A up & B down */
  {
  if (mode= =const_flow)
    {
    FLOWSET=flowset_cf-(flowset_cf/5000L)*TEMPTIME;
```

```
    FLOWSETB=flowset_cf-FLOWSET;
    }
if (mode==const_press)
    {
    PRESSIN=press_set+poffset;
    CONCEN=50000-TEMPTIME*10;
    }
if (!TEMPTIME)
    {
    CNTRL&=0xbf;    /* reset grad mode */
    CNTRLB&=0xfe;   /* stop pump B */
    statusB=stop;
    CNTRLB&=0xbf;   /* reset grad mode */
    access_out&=0x4F; access_out|=0x40;    /* set digital output
                            on a & b */
    ACCESS=access_out;          /* close outlet on pump B */
    flowsum=0;      /* turn off flowrate sum A & B */
    FLOWSET=flowset_cf;
    status=run;
    TEMPTIME=1000;
    PRESSIN=press_set+poffset;
    if (!(sfx_flag & 0x01))
        {
        if (last_Kg==0xA5A5)  /* no previous value to use at startup */
            last_Kg=temp_Kg;
        Kg=(temp_Kg+last_Kg)/2;
        last_Kg=temp_Kg;
        }
    pump_cycle=3;
    }
}
if (pump_cycle==3 && !TEMPTIME)      /* refill B */
    {
    access_out&=0x6F; access_out|=0x60;  /* set digital output
                            on a & b */
    ACCESS=access_out;              /* open inlet on pump B */
    CNTRLB&=0xf9;           /* put B pump in refill */
    CNTRLB|=0x1; statusB=run;
    modeB=refill;
    pump_cycle=4;
    }
if (pump_cycle==4 && lower_limit_B)
    {
    CNTRLB&=0xfe;   /* stop pump B */
    statusB=stop;
    if (!TEMPTIME)
        TEMPTIME=6000;
    if (TEMPTIME < 1000)
        {
        access_out&=0x4F; access_out|=0x40; /* set digital output
                            on a & b */
        ACCESS=access_out;          /* close inlet on pump A & B */
        pressin_temp=PRESS-Kg-1500;
        if ((long)pressin_temp < (long)((PRESS+poffset)/2-Kg))
            pressin_temp=(PRESS+poffset)/2-Kg;
        PRESSINB=pressin_temp;
```

```c
            CNTRLB| =0x6;    /* put pump B in const pressure */
            modeB=const_press;
            CNTRLB| =0x1; statusB=run;   /* run pump B */
            pump_cycle=5;
            }
        }
        if (pump_cycle==5)       /* pre-press pump B & wait for vol. */
        {
        pressin_temp=PRESS-Kg-1500;
        if ((long)pressin_temp < (long)((PRESS+poffset)/2-Kg))
            pressin_temp=(PRESS+poffset)/2-Kg;
        PRESSINB=pressin_temp;

if (get_volM(POSITION,pump_type)<=(max_vol/4)*100  &&
PRESERRB<=5)
            {
            if (!TEMPTIME)
                {
                ACOUNT=0;
                TEMPTIME=10000;
                }
            if (ACOUNT==128)
                {
                ACOUNT=129;
                samp_press=PRESSAVG;
                TEMPTIME=10000;
                pump_cycle=6;
                }
            }
        }
        if (pump_cycle==6)       /* match pressure */
        {
        if (valve_type==1)       /* if active valve */
            PRESSINB=samp_press-Kg;
        else
            PRESSINB=samp_press-Kg-10;
        if ((PRESERRB<=5 && TEMPTIME<5000) || !TEMPTIME)
            {
            if (mode==const_press)
                {
                CONCEN=50000;    /* set concentration to 100% pumpA */
                PINTG=PINTG+PINTGB;
                CNTRL| =0x40;    /* set bit 6 high for grad mode */
                CNTRLB| =0x40;   /* set bit 6 high for grad mode */
                }
            access_out&=0x5F; access_out| =0x50;  /* set digital output
                                on a & b */
            ACCESS=access_out;                    /* open outlet on pump B */
            flowsum=1;         /* add sum of A & B flowrate */
            TEMPTIME=2500;
            pump_cycle=7;
            }
        }
        if (pump_cycle==7)          /* ramp A down & B up to 1/2 flowset */
        {
        if (mode==const_flow)
```

```
    {
    FLOWSETB=flowset_cf/2-(flowset_cf/5000L)*TEMPTIME;
    FLOWSET=flowset_cf-FLOWSETB;
    CNTRLB&=0xfb;   /* put pump B in const flow */
    modeB=const_flow;
    }
  if (mode==const_press)
    CONCEN=10*TEMPTIME+25000;
  if (!TEMPTIME)
    {
    FLOWSETB=FLOWSET=(flowset_cf/2);
    TEMPTIME=20000;
    pump_cycle=8;
    }
  }
  if (pump_cycle==8)   /* measure & adjust B matching factor */
  {
  display_pump=b_pump;
   if (mode==const_flow)
      {
      FLOWSETB=FLOWSET=(flowset_cf/2);
      }
   if (!TEMPTIME)
      {
      ACOUNT=0;
      BCOUNT=0;
      TEMPTIME=10000;
      }
   if (ACOUNT==128)
      {
      ACOUNT=129;
      BCOUNT=129;
      TEMPTIME=2500;
      temp_Kg=PRESSAVG-PRESSAVGB;  /* Kg=difference+
                                         poffset-poffsetB */
      pump_cycle=9;
      }
  }
  if (pump_cycle==9)          /* ramp B up & A down */
  {
  if (mode==const_flow)
    {
    FLOWSETB=flowset_cf-(flowset_cf/5000L)*TEMPTIME;
    FLOWSET=flowset_cf-FLOWSETB;
    }
  if (mode==const_press)
    {
    PRESSINB=press_set-Kg+poffset;
    CONCEN=10*TEMPTIME;
    }
  if (!TEMPTIME)
    {
    PINTGB=PINTG;   /* preset pumpB integrator */
    FLOWSETB=flowset_cf;
    if (!(sfx_flag & 0x01))
        {
```

```
       if (last_Kg= =0xA5A5)  /* no previous value to use at startup */
         last_Kg=temp_Kg;
       Kg=(temp_Kg+last_Kg)/2;
       last_Kg=temp_Kg;
       }
    PRESSINB=press_set-Kg+poffset;
    CNTRL&=0xbf;   /* reset grad mode */
    CNTRLB&=0xbf;  /* reset grad mode */
    CNTRL&=0xfe;   /* stop pump A */
       statusB=run;
       access_out&=0x1F; access_out|=0x10;  /* set digital output
                           on a & b */
        ACCESS=access_out;         /* close outlet on pump A */
        flowsum=0;     /* turn off flowrate sum A & B */
        TEMPTIME=1000;
        pump_cycle=10;
       }
     }
     if (pump_cycle= =10 && !TEMPTIME)       /* refill A */
     {
     access_out&=0x9F; access_out|=0x90;  /* set digital output
                         on a & b */
     ACCESS=access_out;            /* open inlet on pump A */
     CNTRL&=0xf9;          /* put A pump in refill */
     CNTRL|=0x1; status=run;
     pump_cycle=11;
     }
     if (pump_cycle= =11 && lower_limit)
     {
     CNTRL&=0xfe;   /* stop pump A */
     if (!TEMPTIME)
        TEMPTIME=6000;
     if (TEMPTIME < 1000)
       {
       access_out&=0x1F; access_out|=0x10; /* set digital output
                           on a & b */
        ACCESS=access_out;         /* close inlet on pump A */
        pressin_temp=PRESSB+Kg-1500;
        if ((long)pressin_temp < (long)(PRESSB+poffset+Kg)/2)
          pressin_temp=(PRESSB+poffset+Kg)/2;
        PRESSIN=pressin_temp;
        CNTRL|=0x6;          /* put pump A in const pressure */
        CNTRL|=0x1; status=run;  /* run pump A */
        pump_cycle=12;
       }
     }
     if (pump_cycle= =12)    /* pre-press pump A & wait for vol. */
     {
     pressin_temp=PRESSB+Kg-1500;
     if ((long)pressin_temp < (long)(PRESSB+poffset+Kg)/2)
        pressin_temp=(PRESSB+poffset+Kg)/2;
     PRESSIN=pressin_temp;

if   (get_volM(POSITIONB,pump_typeB)< =(max_volB/4)*100   &&
    PRESERR< =5)
         {
```

```
if (!TEMPTIME)
  {
   BCOUNT=0;
   TEMPTIME=10000;
  }
 if (BCOUNT==128)
   {
    BCOUNT=129;
    samp_press=PRESSAVGB;
    TEMPTIME=10000;
    pump_cycle=13;
   }
  }
}
if (pump_cycle==13)          /* match pressure */
{
if (valve_type==1)    /* if active valve */
  {
  if (mode==const_flow)
    PRESSIN=samp_press+Kg;
  else
    PRESSIN=press_set+poffset;
  }
else
  {
  if (mode==const_flow)
    PRESSIN=samp_press+Kg-10;
  else
    PRESSIN=press_set+poffset-10;
  }
if ((PRESERR<=5 && TEMPTIME<5000) || !TEMPTIME)
  {
  if (mode==const_press)
    {
     CONCEN=0;
     PINTG=PINTG+PINTGB;
     CNTRL|=0x40;    /* set bit 6 high for grad mode */
     CNTRLB|=0x40;   /* set bit 6 high for grad mode */
    }
   access_out&=0x5F; access_out|=0x50; /* set digital output
                        on a & b */
   ACCESS=access_out;              /* open outlet on pump A */
   flowsum=1;       /* add sum of A & B flowrate */
   TEMPTIME=2500;
   pump_cycle=14;
  }
}
  if (pump_cycle==14)      /* ramp B down & A up to 1/2 flowset */
  {
  if (mode==const_flow)
    {
     FLOWSET=flowset_cf/2-(flowset_cf/5000L)*TEMPTIME;
     FLOWSETB=flowset_cf-FLOWSET;
     CNTRL&=0xfb;   /* put pump A in const flow */
    }
  if (mode==const_press)
```

```
      CONCEN = 25000-10*TEMPTIME;
    if (ITEMPTIME)
      {
      FLOWSET = FLOWSETB = (flowset_cf/2);
      TEMPTIME = 20000;
      pump_cycle = 1;
      }
    }   /* end of cycle 14 */
  }
  }   /* end of con_flow */
} unsigned press_der(select)
 unsigned char select;
{
static long prev_time;
static unsigned int Pd, prev_data, Pdmax;

if (select = = 0)
  {
  prev_time = REALTIME;
  prev_data = PRESS;
  Pd = Pdmax = 0;
  }
else if ((REALTIME-prev_time) > = 7500)
  {
  Pd = PRESS-prev_data;
  prev_time = REALTIME;
  prev_data = PRESS;
  }
if (Pd > Pdmax)
  Pdmax = Pd;
if (select = = 1)
  return Pd;
else if (select = = 2 && Pd < Pdmax/4 && Pdmax > 4)
  return 1;
else
  return 0;
```

What is claimed is:

1. A supercritical fluid extraction system, comprising:

a supercritical fluid extraction means;

multi-solvent delivery means for supplying a gradient of comparable solvents at a controlled pressure and converting to a pressure vessel communicating with said supercritical fluid extraction means;

said multi-solvent delivery means for supplying including:

a source of a first solvent;

first means for pumping the first solvent through a first pump outlet into a first conduit;

a second solvent;

second means for pumping the second solvent through a second outlet into a second conduit;

first transducer means for measuring the pressure in said first conduit and generating a first signal proportional to the pressure and for measuring the pressure in said second conduit and generating a second signal proportional to the pressure;

mixer means communicating with said first and second conduits for mixing said first and second solvents and applying the mixed solvent solution to said supercritical fluid extraction system;

programmed means for generating third and fourth electrical signals representing programmed concentrations of said first and second solvents respectively in said mixed solvent solution applied to said supercritical fluid extraction system;

means for generating a fifth signal representing a programmed pressure;

means for multiplying said first signal by said third signal, wherein a sixth signal proportional to said pressure in said first conduit multiplied by the programmed concentration of the first solvent in the mixed solvent solution is generated;

means for multiplying said second signal by said fourth signal, wherein a seventh signal proportional to the programmed concentration of said second solvent in the mixed solvent solution multiplied by said pressure in said second conduit is generated;

means for adding said sixth and seventh signals;

feedback comparison means for comparing the sum of said sixth and seventh signals with said signal representing the programmed pressure to generate an error signal;

means for multiplying said error signal by said third signal and supplying it to said first means for pumping to control said pumping rate wherein the pumping rate of the said first means is maintained in programmed concentration proportion to the flow rate at a pressure equal to said programmed pressure; and means for multiplying the error signal by said fourth signal to generate a signal for controlling said second means for pumping, wherein the second means for pumping pumps at a rate of programmed concentration proportion to the flow rate at the programmed pressure, whereby said mixture of solvents is controlled at a programmed concentration of solvents at a programmed pressure.

2. A multi-solvent delivery system comprising:

first means for pumping a first solvent through a first pump outlet into a first conduit;

second means for pumping a second solvent through a second outlet into a second conduit;

first transducer means for measuring pressure in said first conduit and generating a first signal proportional to the pressure;

second transducer means for measuring pressure in said second conduit and converting it to a second pressure signal;

mixer means communicating with said first and second conduits for mixing said first and second solvents and applying the mixed solvents to an outlet port;

programmed means for generating third and fourth electrical signals representing proportions of said first and second solvents in said mixture applied to said mixer outlet port;

means for generating a fifth signal representing programmed pressure;

means for multiplying said first signal by said third signal wherein a sixth signal proportional to said pressure in said first conduit multiplied by the proportion of solvent to be programmed in said first solvent is generated;

means for multiplying said second signal by said fourth signal to generate a seventh signal representing the fraction of said second solvent multiplied by said pressure in said second conduit;

means for adding said sixth and seventh signals;

feedback comparison means for comparing the sum of said sixth and seventh signals with said signal representing the programmed pressure to generate an error signal;

means for multiplying said error signal by said third signal and supplying it to said first means for pumping to control said pumping rate wherein the pumping rate is maintained in concentration proportion to the flow rate at a pressure equal to said programmed pressure; and means for multiplying the error signal by said fourth signal to generate a signal for controlling said second means for pumping wherein the second means for pumping pumps at a rate in concentration proportion to the flow rate at a pressure equal to the said programmed pressure, whereby said mixture of solvents is controlled in a programmed concentration of solvents at a programmed pressure.

3. A method of supplying a supercritical system with a programmed plurality of solvents comprising the steps of:

pumping a first fluid with a first pump up to a valve upstream of the supercritical system;

pumping a second fluid from a second pump to the same valve;

measuring pressure in a first conduit connecting an outlet port of said first pump to said valve to obtain a first signal;

measuring pressure in a second conduit between an outlet port of the second pump and the valve to obtain a second signal;

multiplying the first signal by a third signal representing the concentration of the first fluid in the total fluid mixture to obtain a fourth signal;

multiplying the second signal by a program signal; representing the concentration of the second fluid in the total mixture to generate a fifth signal;

comparing said fourth signal with a pressure reference point and using an error signal to control said first pump, whereby the first fluid is controlled; and comparing the fourth signal with said pressure reference point and using the error signal to control said second pump whereby the second fluid is controlled.

4. A fluid control system comprising:

a plurality of pumps delivering fluid into a common mixing conduit;

a back-flow-preventing check valve between the pump fluid outlet and the mixer on all but one of the pumps which is the primary fluid delivery pump;

means to control the pressurization of said pumps so as to ramp the pressures of the secondary pumps to match the pressure of the primary fluid delivery pump;

pressure transducer means for measuring the pressure in the common mixing conduit downstream of the back flow preventing check valves and generating a signal proportional to the pressure;

means for detecting fluctuations of said pressure signal indicating the pressure equalization of a secondary pump; and means to control the fluid delivery of the pumps at a controlled pressure or flow rate after the pressure are detected to be equal.

5. A fluid control system comprising:

at least first and second pump means;

a first fluid source adapted to be pumped by said first pump means;

a second fluid source adapted to be pumped by said second pump means;

a first fluid output line connected to said first pump means;

a second fluid output line connected to said second pump means;

a first check valve adapted to permit flow from said first output line into a mixer;

a second check valve adapted to permit flow from said second output line to said mixer;

a first pressure transducer in said first output line;

a second pressure transducer in said second output line;

means for detecting a sudden change in a characteristic of the pressure from one of said first and second transducers, whereby a signal is provided indicating an opening of a check valve; and means for starting a refill cycle of one of said first and second pumps in timed relation with detection of said signal.

6. A fluid control system comprising:

at least first and second pump means;

a first fluid source adapted to be pumped by said first pump means;

a second fluid source adapted to be pumped by said second pump means;

a first fluid output line connected to said first pump means;

a second fluid output line connected to said second pump means;

a first check valve adapted to permit flow from said first output line into a mixer;

a second check valve adapted to permit flow from said second output line to said mixer;

a first pressure transducer in said first output line;

a second pressure transducer in said second output line; and means for detecting a sudden change in a characteristic of the pressure from one of said first and second transducers, whereby an opening of a check valve is detected.

7. A fluid control system according to claim 6 in which the detected opening of a check valve causes the speed of a corresponding pump to be changed to a programmed pumping rate.

8. A fluid control system comprising:

a plurality of pumps;

a corresponding plurality of check valves; and means for causing delivery pressures of at least two of said plurality of pumps to match by detecting that their corresponding opening to a common fluid port have opened;

said means for causing delivery pressures of at least two of said plurality of pumps to match includes means for forcing the pressures to match by connecting pressure transducers to the common fluid port by means of a manual or automatic valve.

9. A fluid control system according to claim 8 in which said means for causing delivery pressures of at least two of said plurality of pumps to match by detecting that their corresponding check valves to a common fluid port have opened comprises means for forcing said check valves to open by pumping fluid through the check valves.

10. A fluid control system comprising:

a plurality of pumps;

a corresponding plurality of check valves; and means for causing delivery pressures of at least two of said plurality of pumps to match by detecting that their corresponding opening to a common fluid port have opened; and means for adjusting the pressures signals of a plurality of transducers to match wile the pumps are known to be at the same delivery pressure.

11. A fluid control system according to claim 10 further including means for using the pressure matching information to shorten the time and improve the accuracy of pressure matching for the purpose of equilibrating pressures from pump stroke to pump stroke in a multiple pump fluid delivery system.

12. A method of applying solvent to a supercritical fluid system comprising the steps of:

applying a first fluid from a first pump to a valve located upstream of the supercritical fluid system until pressure in the flow path reaches a predetermined setpoint pressure value;

controlling the pressure of the first fluid by a feedback circuit from a transducer in the flow path between a second pump and the valve at said setpoint pressure;

automatically opening said valve to permit the flow to the downstream side of said supercritical fluid system; and pumping fluid until pressure has stabilized and continuing the pumping until the supercritical process is completed.

13. A method according to claim 12 further comprising the steps of:

blocking said fluid downstream of said supercritical fluid system with a second valve;

pumping a second fluid to a pressure a predetermined increment of pressure below a preset pressure;

opening said second valve; and increasing the pressure of said second fluid to said preset pressure value, wherein the pressure of said second fluid is controlled by a feedback system having a transducer in the flow path between the second pump and said first valve.

14. A method in accordance with claim 13 further including the step of pumping the first and second fluids in a constant flow mode after said first and second fluids are flowing and said second valve has been opened.

15. A method in accordance with claim 13 further including the step of pumping the first and second fluids in a constant pressure mode after said first and second fluids are flowing and said second valve has been opened.

16. A method in accordance with claim 13 wherein the step of controlling the second pump includes the substeps of multiplying pressure in a conduit between said second pump and said first valve by a programmed proportion of final fluid mixture to be sent to the supercritical system which is a ratio of said second fluid to the programmed total fluid to form a product, comparing the product to the setpoint value and controlling the pumping rate of pumping of said first pump with an error signal from the comparison multiplied by the proportion of said first fluid to the total fluid.

17. A fluid control system comprising:

at least first and second pump means;

a first fluid source adapted to be pumped by said first pump means;

a second fluid source adapted to be pumped by said second pump means;

a first outlet conduit connected to said first pump means;

a second outlet conduit connected to said second pump means;

means for combining fluid flow from said first and second conduits to obtain combined fluids;

means for obtaining a first signal representing a pressure of the combined fluids;

means for comparing the first signal with a reference pressure signal to obtain an error signal;

program means for generating a second signal representing a programmed concentration of the first fluid in the combined fluids to be pumped by said first pump means into said first conduit and for generating a third signal representing a programmed concentration of the second fluid in the combined fluids to be pumped by said second pump means into said second conduit;

means for multiplying said error signal by said second signal to obtain a fourth signal and using said fourth signal to control a pumping rate of the first pump means; and means for multiplying said error signal by said third signal to obtain a fifth signal and using the fifth signal to control a flow rate of said second pump means, whereby the concentration and pressure of said combined fluids is controlled.

18. A fluid control system in accordance with claim 17 in which:

said means for generating a signal representing the pressure of said combined fluids includes a first transducer means for measuring the pressure in the first outlet conduit of said first pump means;

means for multiplying said pressure signal by said third signal;

second transducer means for measuring the outlet pressure of said second pump means;

means for multiplying a signal from said second transducer means by the fourth signal; and means for combining said third and fourth signals, whereby a signal representing the pressure of the combined flow rates is obtained from pressure signals at the outlet of each of a plurality of pumps.

19. A fluid control system in accordance with claim 17 in which the fluid control system is adapted to supply fluid to an apparatus for utilizing the fluid and the fluid control system includes:

a first valve in a flow circuit between said means for combining fluid flow and said apparatus utilizing the fluid; and means for closing said valve during start-up of the fluid control system.

20. A fluid control system in accordance with claim 19 further including a second valve means communicating with an outlet of said apparatus for utilizing said fluids adapted to be closed during a second stage of the start-up procedure of said fluid control system.

21. A fluid control system in accordance with claim 20 further comprising:

a first check valve connected to said first outlet conduit downstream of said means for obtaining a first signal and upstream of said means for combining fluid flow from said first and second conduits; and second check valve means communicating with said second outlet conduit downstream from said means for obtaining a second signal and upstream from said means for combining fluids, whereby said first and second check valves permit flow from said first and second outlet conduit means into said means for combining fluids and restrict flow from said means for combining fluids to said first and second pump means respectively.

22. A fluid control system according to claim 21 further including means for detecting when said first outlet conduit reaches the programmed pressure and beginning an increase in pressure in said second outlet conduit.

* * * * *